(12) United States Patent
Miele

(10) Patent No.: US 6,554,774 B1
(45) Date of Patent: Apr. 29, 2003

(54) METHOD AND APPARATUS FOR ASSESSING HEMODYNAMIC PROPERTIES WITHIN THE CIRCULATORY SYSTEM OF A LIVING SUBJECT

(75) Inventor: Frank R. Miele, Methuen, MA (US)

(73) Assignee: Tensys Medical, Inc., San Diego, CA (US)

( * ) Notice: Subject to any disclaimer, the term of this patent is extended or adjusted under 35 U.S.C. 154(b) by 0 days.

(21) Appl. No.: 09/534,900

(22) Filed: Mar. 23, 2000

(51) Int. Cl.$^7$ ................................ A61B 5/00
(52) U.S. Cl. ............... 600/485; 600/490; 600/500; 600/504
(58) Field of Search ............... 600/485, 480, 600/493–6, 500–505

(56) References Cited

U.S. PATENT DOCUMENTS

| | | |
|---|---|---|
| 3,601,120 A | 8/1971 | Massie et al. |
| 3,617,993 A | 11/1971 | Massie et al. |
| 3,663,932 A | 5/1972 | Mount et al. |
| 3,791,378 A | 2/1974 | Hochbert et al. |
| 3,885,551 A | 5/1975 | Massie |
| 4,109,647 A | 8/1978 | Stern et al. |
| 4,127,114 A | 11/1978 | Bretscher |
| 4,154,231 A | 5/1979 | Russell |
| 4,239,047 A | 12/1980 | Griggs, III et al. |
| 4,249,540 A | 2/1981 | Koyama et al. |
| 4,349,034 A | 9/1982 | Ramsey, III |
| 4,476,875 A | 10/1984 | Nilsson et al. |

(List continued on next page.)

FOREIGN PATENT DOCUMENTS

| | | |
|---|---|---|
| EP | 284 095 B1 | 3/1988 |
| EP | 0 342 249 A1 | 5/1988 |
| EP | 0595 666 B1 | 9/1993 |
| EP | 0 603 666 A2 | 12/1993 |
| EP | 0818 176 A | 7/1996 |
| WO | WO 84 00290 | 2/1984 |
| WO | WO 92/07508 | 10/1991 |
| WO | WO 95 13014 | 5/1995 |
| WO | WO 98 25511 A | 6/1998 |

OTHER PUBLICATIONS

Anderson, E.A., et al. (1989) "Flow–Mediated and Reflex Changes in Large Peripheral Artery Tone in Humans," Circulation 79:93–100.

(List continued on next page.)

*Primary Examiner*—Robert L. Nasser
(74) *Attorney, Agent, or Firm*—Gazdzinski & Associates

(57) ABSTRACT

An improved method and apparatus for non-invasively assessing one or more hemodynamic parameters associated with the circulatory system of a living organism. In one aspect, the invention comprises a method of measuring a hemodynamic parameter by measuring a non-calibrated value of the parameter non-invasively, and inducing a stress of the circulatory system while measuring a second parameter. The response of the circulatory system to the stress is determined directly from the subject, and a calibration function is derived from the response and applied to the non-calibrated measured value to produce a calibrated measure of the actual value of the hemodynamic parameter. Methods of generating a tissue transfer function from measurements of the subject, correcting for periodic or aperiodic error components, and providing treatment to the subject based on the measured hemodynamic parameters, are also disclosed.

43 Claims, 21 Drawing Sheets

U.S. PATENT DOCUMENTS

| | | | |
|---|---|---|---|
| 4,566,462 | A | 1/1986 | Janssen |
| 4,590,948 | A | 5/1986 | Nilsson |
| 4,596,254 | A | 6/1986 | Adrian et al. |
| 4,651,747 | A | 3/1987 | Link |
| 4,719,923 | A | 1/1988 | Hartwell et al. |
| 4,754,761 | A | 7/1988 | Ramsey, III et al. |
| 4,771,792 | A | 9/1988 | Seale |
| 4,867,170 | A | 9/1989 | Takahashi |
| 4,869,261 | A | 9/1989 | Penaz |
| 4,880,013 | A | 11/1989 | Chio |
| 4,901,733 | A | 2/1990 | Kaida et al. |
| 4,924,871 | A | 5/1990 | Honeyager |
| 4,960,128 | A | 10/1990 | Gordon et al. |
| 5,030,956 | A | 7/1991 | Murphy |
| 5,072,733 | A | 12/1991 | Spector et al. |
| 5,094,244 | A | 3/1992 | Callahan et al. |
| 5,119,822 | A | 6/1992 | Niwa |
| 5,152,297 | A * | 10/1992 | Meister et al. .............. 600/485 |
| 5,158,091 | A | 10/1992 | Butterfield et al. |
| 5,163,438 | A | 11/1992 | Gordon et al. |
| 5,170,796 | A | 12/1992 | Kobayashi |
| 5,238,000 | A | 8/1993 | Niwa |
| 5,240,007 | A | 8/1993 | Pytel et al. |
| 5,261,412 | A | 11/1993 | Butterfield et al. |
| 5,273,046 | A | 12/1993 | Butterfield et al. |
| 5,368,039 | A | 11/1994 | Moses |
| 5,406,952 | A | 4/1995 | Barnes et al. |
| 5,439,001 | A | 8/1995 | Butterfield et al. |
| 5,450,852 | A | 9/1995 | Archibald et al. |
| 5,467,771 | A | 11/1995 | Narimatsu et al. |
| 5,479,928 | A | 1/1996 | Cathignol et al. |
| 5,494,043 | A | 2/1996 | O'Sullivan et al. |
| 5,533,511 | A | 7/1996 | Kaspari et al. |
| 5,590,649 | A | 1/1997 | Caro et al. |
| 5,617,867 | A | 4/1997 | Butterfield et al. |
| 5,634,467 | A | 6/1997 | Nevo |
| 5,642,733 | A | 7/1997 | Archibald et al. |
| 5,649,542 | A | 7/1997 | Archibald et al. |
| 5,649,543 | A * | 7/1997 | Hosaka ....................... 600/500 |
| 5,832,924 | A | 11/1998 | Archibald et al. |
| 5,833,618 | A | 11/1998 | Caro et al. |
| 5,848,970 | A | 12/1998 | Voss et al. |
| 5,876,346 | A | 3/1999 | Corso |
| 5,882,311 | A * | 3/1999 | O'Rourke ................... 600/500 |
| 5,895,359 | A | 4/1999 | Peel, III |
| 5,908,027 | A | 6/1999 | Butterfield et al. |
| 5,916,180 | A | 6/1999 | Cundari et al. |
| 5,964,711 | A | 10/1999 | Voss et al. |
| 6,010,457 | A * | 1/2000 | O'Rourke ................... 600/500 |
| 6,027,452 | A * | 2/2000 | Flaherty et al. ............. 600/500 |
| 6,176,831 | B1 | 1/2001 | Voss et al. |
| 6,228,034 | B1 | 5/2001 | Voss et al. |
| 6,270,461 | B1 | 8/2001 | Chio |
| 6,340,439 | B1 | 1/2002 | Archibald et al. |
| 6,371,921 | B1 * | 4/2002 | Caro et al. .................. 600/500 |

OTHER PUBLICATIONS

Boashash, B., et al. (1987) "An Efficient Real–Time Implementation of the Wigner–Ville Distribution," IEEE Trans ASSP 35:1611–1618.

Drzewiecki, G.M., et al. (1985) Generalization of the Transmural Pressure–Area Relation for the Femoral Artery, $7^{th}$ Annual IEEE EMBS Conference 507.

Hoeks, A.P.G., et al. (1985) Transcutaneous Detection of Relative Changes in Artery Diameter, Ultrasound in Med and Bio 11:51–59.

Carson, E.R., et al. (1983) "The Mathematical Modeling of Metabolic and Endocrine Systems: Model Formulation, Identification, and Validation," John Wiley & Sons, NY, pp. 185–189.

Drzewiecki, G. (1995) "Noninvasive Assessment of Arterial Blood Pressure and Mechanics," The Biomedical Engineering Handbook CRC Press, Boca Raton, FL, pp. 1196–1211.

Hartley, C.J., et al. (1991) "An Ultrasonic Method for Measuring Tissue Displacement: Technical Details and Validation for Measuring Myocardial Thickening," IEEE Trans Biomed, 38:735–747.

Cariou, Alain, et al. (1998) "Noninvasive Cardiac Output Monitoring by Aortic Blood Flow Determination: Evalution of the Sometec Cynemo–3000 System," Critical Care Medicine, vol. 26, No. 12, pp. 2066–2072.

Advertisement for HemoSonic™ 100 by Arrow International—licensed under U.S. Patent 5,479,928 listed above.

Mehra, Mandeep R., et al. (May/Jun. 2000) "Emergence of Electronic Home Monitoring In Chronic Heart Failure: Rationale, Feasibility, and Early Results with the Hom/Med Sentry–Observer System," (consisting of 3 pages).

Application Serial No. 09/342,542 entitled "Method and Apparatus for the Noninvasive Determination of Arterial Blood Pressure," filed Jun. 29, 1999—Attorney Docket No. VWAVE.001A (refers to time–frequency methodology).

* cited by examiner

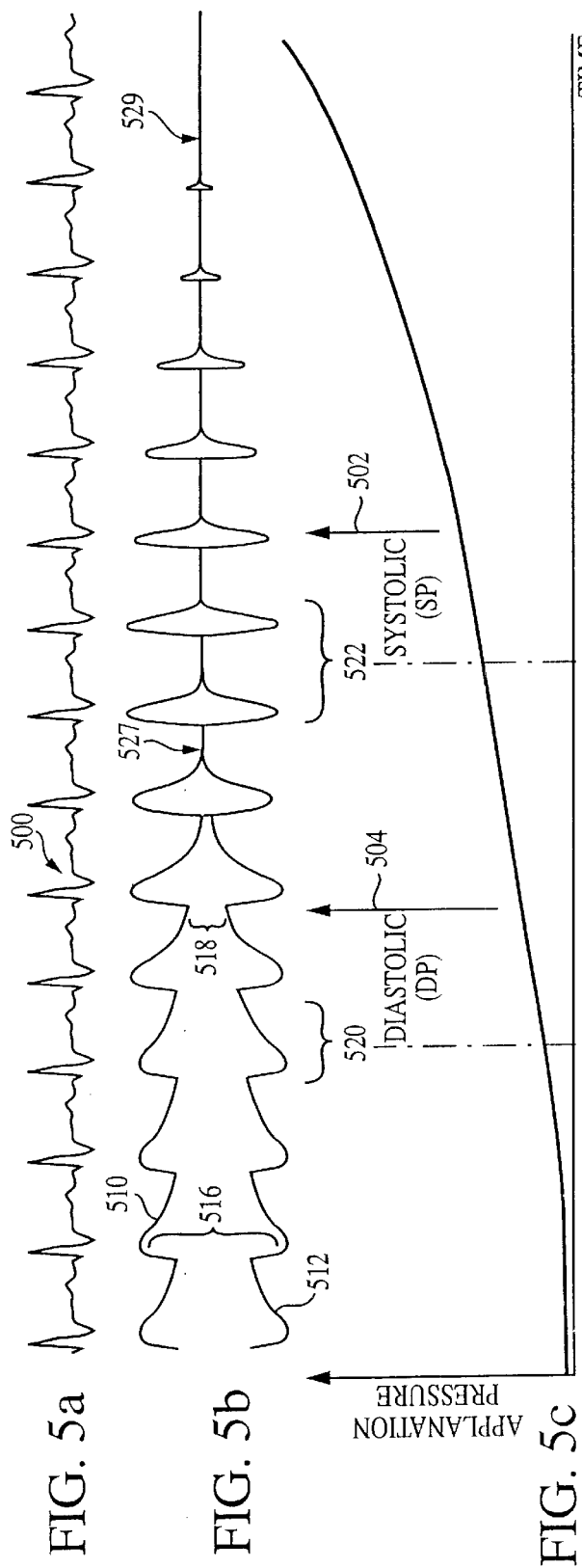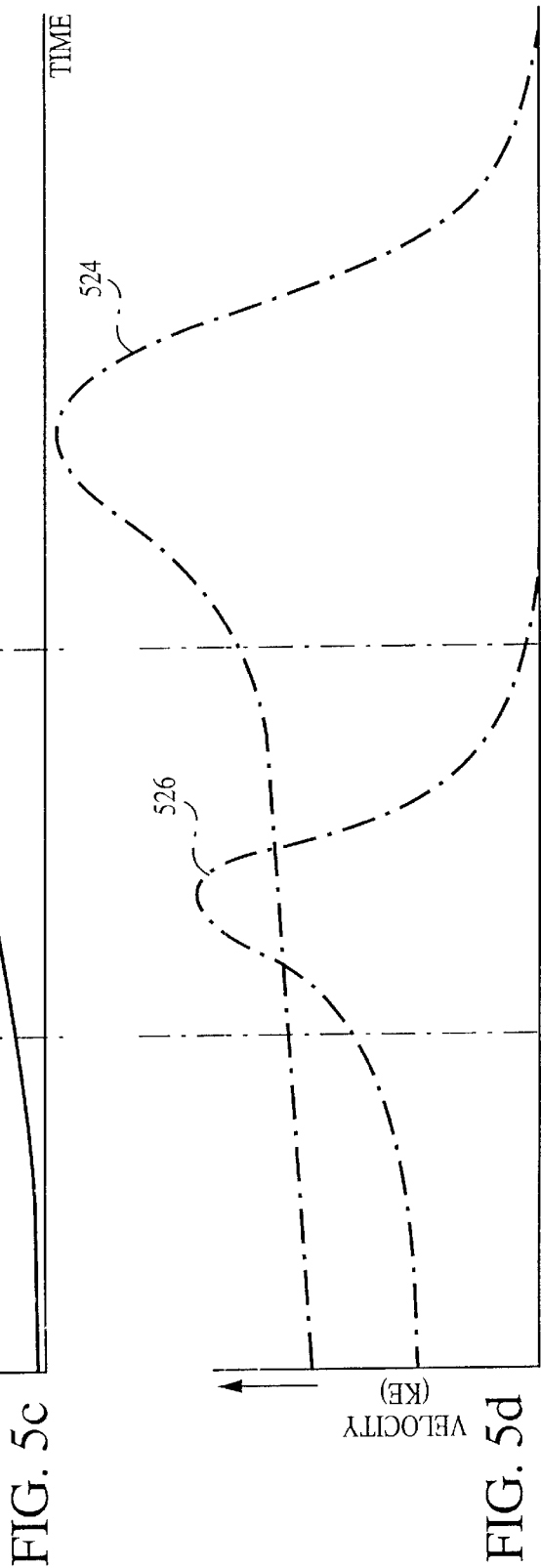

METHOD AND APPARATUS FOR ASSESSING HEMODYNAMIC PROPERTIES WITHIN THE CIRCULATORY SYSTEM OF A LIVING SUBJECT

BACKGROUND OF THE INVENTION

1. Field of the Invention

This invention relates generally to methods and apparatus for monitoring parameters associated with the circulatory system of a living subject, and specifically to the non-invasive monitoring of arterial blood pressure.

2. Description of Related Technology

Arterial Blood Pressure Measurement

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. This theory is illustrated graphically in FIG. 1. Note that in FIG. 1, bone or another rigid member is assumed to lie under the artery.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement.

Tonometry systems are also commonly quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches to lateral sensor positioning similarly suffer from not being able to maintain a constant angular relationship with the artery regardless of lateral position, due in many cases to positioning mechanisms which are not adapted to account for the anatomic features of the subject, such as curvature of the wrist surface.

Another significant drawback to arterial tonometry systems in general is their inability to continuously monitor and adjust the level of arterial wall compression to an optimum level of zero transmural pressure. Generally, optimization of arterial wall compression has been achieved only by periodic recalibration. This has required an interruption of the subject monitoring function, which sometimes can occur during critical periods. This disability severely limits acceptance of tonometers in the clinical environment.

A further limitation of the tonometry approach relates to incomplete pressure pulse transfer from the interior of the blood vessel to the point of measurement on the surface of the skin above the blood vessel. Specifically, even when the optimum level of arterial compression is achieved, there is incomplete and complex coupling of the arterial blood pressure through the vessel wall and through the tissue, to the surface of the skin, such that the magnitude of pressure variations occurring within the blood vessel is different than that measured by a tonometric sensor (pressure transducer) placed on the skin. Hence, any pressure signal or waveform measured at the skin necessarily differs from the true pressure within the artery. Modeling the physical response of the arterial wall, tissue, musculature, tendons, bone, skin of the wrist is no small feat, and inherently includes uncertainties and anomalies for each separate individual. These uncertainties and anomalies introduce unpredictable error into any measurement of blood pressure made via a tonometric sensor.

One prior art method of calibrating tonometric pressure measurements utilizes an oscillometric device (i.e., a pressure cuff or similar) to periodically obtain "actual" pressure information which is then used to calibrate the tonometric measurements. This approach suffers from the need to perform ongoing calibration events, specifically inflations/ deflations of the cuff, in order to maintain device calibration. Such calibration events are distracting, uncomfortable, and can practically only be performed with a comparatively long periodicity. Furthermore, this technique does not calibrate based on measurement of actual hemodynamic changes occurring within the circulatory system, but rather based on external measurements which may or may not be representative of the actual changes. No mechanism for correcting for incomplete pulse transfer from the blood vessel to the sensor(s) due to interposed tissue, etc. is provided either.

Other prior art calibration techniques have attempted to transmit or induce a perturbation within the blood flowing in the blood vessel, and subsequently sense the component of that signal within the measured hemodynamic parameter (e.g., blood pressure waveform) to generate an offset or correction for the measured parameter. See, for example, U.S. Pat. No. 5,590,649 entitled "Apparatus and Method for Measuring an Induced Perturbation to Determine Blood Pressure" assigned to Vital Insite, Inc. ('649 patent). Under the approach of the '649 patent, changes in a variety of hemodynamic parameters resulting ostensibly from changes in blood pressure are modeled and stored within the device, and compared to data obtained from a tonometric sensor. This approach, however, has a profound disability in that the calibration offset is determined not by direct measurement of the hemodynamic parameters of the subject under evaluation, but by modeling the relationship between blood pressure and perturbation wave velocity; i.e., velocity and phase are modeled to have a certain relationship to changes in blood pressure; therefore, in theory, observed changes in velocity/phase of the perturbation wave can be used to generate estimations of actual blood pressure within the subject being evaluated. The limits of this system are clearly dictated by the ability to accurately model many complex, non-linear, interdependent parameters, as well as predict the time variance of these many parameters.

Hemodynamics and Diseases of the Circulatory System

The science of hemodynamics, or the analysis of fluid (blood) flow within the body, is presently used effectively to detect and/or diagnose diseases of or defects within the circulatory system. For example, valvular disease, cardiac structural defects, venous disease, reduced cardiac function, and arterial disease may be assessed by studying how the blood flows through various portions of the circulatory system. Of particular interest is the analysis of arterial diseases such as stenosis (i.e. blockage or reduction in effective cross-sectional area due to arterial plaque, etc.). It is known that as the degree of stenosis within the blood vessel of a living subject varies, certain changes in the parameters of the circulatory system and in the overall health of the subject occur. As illustrated in FIG. 2, varying degrees of stenosis within a hypothetical blood vessel will occlude that blood vessel to a generally proportional degree; i.e., no stenosis results in no occlusion and no attendant symptoms, while complete stenosis results in complete occlusion, with no flow of blood through the vessel and very dire symptoms in the subject. At levels of stenosis falling somewhere there between, the response can be somewhat more complex. For example, the subject may suffer stenosis which very significantly reduces the effective cross-sectional area of a given blood vessel, yet manifests itself in very few if any symptoms under normal levels of exercise. However, the same subject can exhibit dramatic symptoms with an increase in exercise. as the patient exerts more effort, the tissue under exertion has a higher metabolic demand requiring an increase in perfusion. Normally, vasodilation and collateralized blood flow provide the compensatory mechanism to increase the volumetric flow to meet the higher volumetric demand. However, since the vessel is significantly stenosed, the compensatory mechanism has already been utilized to meet the normal, non-exercise demand. As a result, the body is unable to increase the volumetric demand since it has no way of minimizing the energy loss associated with overcoming the resistance of the stenosed (decreased) area of the vessel. If volumetric flow does not increase, the increased metabolic demand is not met and the distal tissue becomes ischemic.

By modeling the stenotic artery as a fluid system having an internal pressure (P) and blood mass flow rate (Q) or blood velocity (v), a modified version of the well known Bernoulli equation may be applied to describe the flow of blood within the artery as follows:

$$\Delta P \; 4 \cdot v^2 \qquad \text{Eqn. (1)}$$

Hence, the foregoing relationship may be used to assess one hemodynamic parameter when another is known. For example, the pressure gradient ($\Delta P$) across a stenosis within the artery may be estimated by obtaining data on the velocity of blood flowing through the stenosis, and then using this velocity data within Eqn. (1). The velocity data may be obtained by any number of well known techniques, such as spectral Doppler ultrasound.

However, despite their utility in assessing the severity of stenoses present in the artery and other such diseases, prior art hemodynamic evaluation techniques are effectively incapable of assessing the absolute blood pressure within the artery at any given time. In theory, an accurate model of the response of the circulatory system could be used to estimate the value of parameters within the system (such as true arterial pressure) based on known or measured values of other parameters. As can be appreciated, however, the circulatory system of a living organism, and especially a human being, is extremely complex, with literally thousands of interconnected blood vessels. This system includes, inter alia, scores of capillaries, veins, and arteries, each having their own unique physical properties. Furthermore, within each of the aforementioned categories of blood vessel, individual constituents may have markedly different properties and response within the circulatory system. For example, two arteries within the human body may (i) have different diameters at different points along their length; (ii) supply more or less veins and capillaries than the other; (iii) have more or less elasticity; and (iv) have more or less stenosis associated therewith.

The properties and response of each of the blood vessels also may be affected differently by various internal and/or external stimuli, such as the introduction of an anesthetic into the body. Even common autonomic responses within the body such as respiration affect the pressure in the circulatory system, and therefore may need to be considered.

Considering these limitations, it becomes exceedingly difficult if not impossible to accurately model the circulatory system of the human being in terms of its fluid dynamic properties for use in blood pressure estimation. Even if a hypothetical circulatory system could be accurately modeled, the application of such a model would be susceptible to significant variability from subject to subject due to each subject's particular physical properties and responses. Hence, such approaches can at best only hope to form gross approximations of the behavior of the circulatory system, and accordingly have heretofore proven ineffective at accurately determining the blood pressure within a living subject.

Based on the foregoing, what is needed is an improved method and apparatus for assessing hemodynamic parameters, including blood pressure, within a living subject. Such method and apparatus would ideally be non-invasive, would be continuously or near-continuously self-calibrating, and would be both useful and produce reliable results under a variety of different subject physiological circumstances, such as when the subject is both conscious and anesthetized. Lastly, such improved method and apparatus would be based primarily on parameters measured from each particular subject being assessed, thereby allowing for calibration unique to each individual.

SUMMARY OF THE INVENTION

The present invention satisfies the aforementioned needs by an improved method and apparatus for assessing hemodynamic properties, including blood pressure, within a living subject.

In a first aspect of the invention, a method of assessing hemodynamic properties including blood pressure within the circulatory system is disclosed. The method generally comprises the steps of: measuring a first parameter from the blood vessel of a subject; measuring a second parameter from the blood vessel; deriving a calibration function based on the second parameter; and correcting the first parameter using the derived calibration function. Once calibrated, the second parameter is monitored continuously or periodically; changes in that parameter are used to indicate changes in the hemodynamic property of interest. In a first exemplary embodiment, the first parameter comprises a pressure waveform, and the second parameter comprises the total flow kinetic energy of blood within the blood vessel. During measurement of the pressure waveform, the blood vessel is applanated (compressed) so as to induce changes in the hemodynamic properties within the blood vessel and circulatory system; the kinetic energy during such applanation is then measured and used to identify one or more artifacts within the pressure waveform. A correction function is then generated based on these artifacts, and applied to the measured pressure waveform to generate a corrected or calibrated waveform representative of the actual pressure within the blood vessel. In a second exemplary embodiment, the maximal velocity of the blood flowing within the blood vessel is determined using an acoustic signal and used to derive a calibration function.

In a second aspect of the invention, an improved method of calibrating a pressure signal obtained from a blood vessel of a living subject using one or more measured parameters is disclosed. Generally, the method comprises: measuring a pressure waveform from the blood vessel; measuring a second parameter at least periodically from the blood vessel; deriving a calibration function based on the second parameter; and correcting the first parameter using the derived calibration function. In one exemplary embodiment, the method comprises measuring the pressure waveform from a blood vessel of the subject; measuring a second parameter from the same blood vessel at least once; identifying at least one artifact within the pressure waveform based on the second parameter; deriving a calibration function based on the measured second parameter and at least one property associated with the at least one artifact; applying the calibration function at least once to the pressure waveform to generate a calibrated representation of pressure within the blood vessel; and continuously monitoring the second parameter to identify variations in blood pressure with time.

In a third aspect of the invention, an improved method of characterizing the hemodynamic response of the circulatory system of a living subject is disclosed. The method generally comprises the steps of: deriving a first functional relationship between first and second parameters associated with a blood vessel under certain conditions; measuring the first and second parameters non-invasively under those certain conditions; identifying at least one artifact within at least one of the measured parameters; and scaling the measurement of the first parameter based on at least the first functional relationship and the at least one artifact.

In a fourth aspect of the invention, an improved method of calibrating a hemodynamic parametric measurement having an error component is disclosed. Generally, the method comprises measuring a hemodynamic parameter associated with a blood vessel; identifying an error source associated with the first parameter; generating a calibration function based on the error source; and correcting the measured hemodynamic parameter using the calibration function. In one exemplary embodiment, the method comprises measuring a pressure waveform from the blood vessel; identifying a periodic variation associated with the kinetic energy (or maximal velocity) of the blood within the blood vessel over time due to respiratory effects; generating a calibration function based on synchronization with the variation in kinetic energy over time; and applying the calibration function to the pressure waveform to correct the waveform for the periodic variation. This respiratory effect is also detectable from the pressure signal, and potentially other signals as well.

In a fifth aspect of the invention, an improved apparatus for measuring hemodynamic properties within the blood vessel of a living subject is disclosed. The apparatus generally a first transducer for measuring a first hemodynamic parameter associated with the blood vessel; a second transducer for measuring a second hemodynamic parameter associated with the blood vessel; and a signal processor operatively connected to the first and second transducers for generating a calibration function based on the signal produced by the second transducer, and applying the correction function to the signal produced by the first transducer. In one exemplary embodiment, the blood vessel comprises the radial artery of a human being, and the apparatus comprises a pressure transducer disposed non-invasively in proximity thereto; an acoustic transducer also disposed in proximity thereto; an applanation device used to applanate the blood vessel; and a processor for processing signals from the pressure and acoustic transducers during applanation of the blood vessel. The acoustic transducer transmits an acoustic emission into the blood vessel and receives an echo therefrom; information regarding the blood's velocity and/or kinetic energy during the applanation is derived from the echo and used to generate a correction function which is then applied to the measured pressure waveform to calibrate the latter.

In a sixth aspect of the invention, an improved computer program for implementing the aforementioned methods of hemodynamic assessment, modeling, and calibration is disclosed. In one exemplary embodiment, the computer program comprises an object code representation of a $C^{++}$ source code listing, the object code representation is disposed on the storage device of a microcomputer system and is adapted to run on the microprocessor of the microcomputer system. The computer program further comprises a graphical user interface (GUI) operatively coupled to the display and input device of the microcomputer. One or more subroutines or algorithms for implementing the hemodynamic assessment, modeling, and calibration methodology described herein based on measured parametric data provided to the microcomputer are included within the program. In a second exemplary embodiment, the computer program comprises an instruction set disposed within the storage device (such as the embedded program memory) of a digital signal processor (DSP) associated with the foregoing hemodynamic measurement apparatus.

In an seventh aspect of the invention, an improved apparatus for analyzing parametric data obtained according to the foregoing methods and utilizing the aforementioned computer program is disclosed. In one exemplary embodiment, the apparatus comprises a microcomputer having a processor, non-volatile storage device, random access memory, input device, display device, and serial/parallel data ports operatively coupled to one or more sensing devices. Data obtained from a subject under analysis is input to the microcomputer via the serial or parallel data port; the object code representation of the computer program stored on the storage device is loaded into the random access memory of the microcomputer and executed on the processor as required to analyze the input data in conjunction with commands input by the user via the input device.

In a eighth aspect of the invention, an improved method of providing treatment to a subject using the aforementioned method is disclosed. The method generally comprises the steps of: selecting a blood vessel of the subject useful for measuring pressure data; measuring the pressure data of the subject non-invasively; generating a calibration function; applying the calibration function to the measured pressure data to produce a calibrated representation of blood pressure within the blood vessel; and providing treatment to the subject based on the calibrated estimate. In one exemplary embodiment, the blood vessel comprises the radial artery of the human being, and the method comprises measuring a pressure waveform from the radial artery via a pressure transducer; using an acoustic wave to measure at least one hemodynamic parameter; deriving a calibration function based at least in part on the measured hemodynamic parameter; calibrating the pressure waveform using the calibration function to derive a calibrated representation of blood pressure useful for diagnosing one or more medical conditions within the subject; and providing a course of treatment to the subject based at least in part on the calibrated representation.

BRIEF DESCRIPTION OF THE DRAWINGS

FIGS. 5a–5c are graphs illustrating the relationship between applanation pressure, cardiac sinus rhythm, and arterial wall displacement according to the invention.

FIG. 5d is a graph illustrating the relationship between maximum blood velocity and percentage reduction in flow area (applanation pressure) for both diastolic and systolic pressures.

DETAILED DESCRIPTION OF THE INVENTION

Reference is now made to the drawings wherein like numerals refer to like parts throughout.

It is noted that while the invention is described herein in terms of a method and apparatus for assessing the hemodynamic parameters of the circulatory system via the radial artery (i.e., wrist) of a human subject, the invention may also be embodied or adapted to monitor such parameters at other locations on the human body, as well as monitoring these parameters on other warm-blooded species. All such adaptations and alternate embodiments are considered to fall within the scope of the claims appended hereto.

Overview

In one fundamental aspect, the present invention comprises a method of assessing hemodynamic parameters within a living subject by artificially inducing "stresses" on the subject's circulatory system. The response of the circulatory system to these stresses is known or determinable, and useful in identifying artifacts or markers with the observed data. These markers are subsequently used to calibrate measurements of the aforementioned hemodynamic parameters.

For example, as will be described in greater detail below, the present invention is useful at calibrating the blood pressure waveform obtained from a tonometric or surface pressure sensor disposed over the radial artery of a human being, the non-calibrated pressure waveform potentially varying substantially from that actually experienced within the radial artery itself. In one embodiment, the "stress"

placed on the artery is applanation (i.e., compression), and the velocity of blood flowing through the area of applanation is monitored to identify markers within the velocity profile. These markers correspond to, inter alia, a state of near zero transmural pressure across the artery wall. In this fashion, an accurate measure of true arterial pressure may be obtained non-invasively. It will be recognized, however, that the invention as described herein may also be readily used in assessing other hemodynamic properties, such as the pressure differential between two locations within a blood vessel, venous or arterial wall compliance, variations in the strength of ventricular contraction, and the like, and accordingly is not limited to the measurement of arterial blood pressure.

Method of Assessing Hemodynamic Properties

Figure 1:
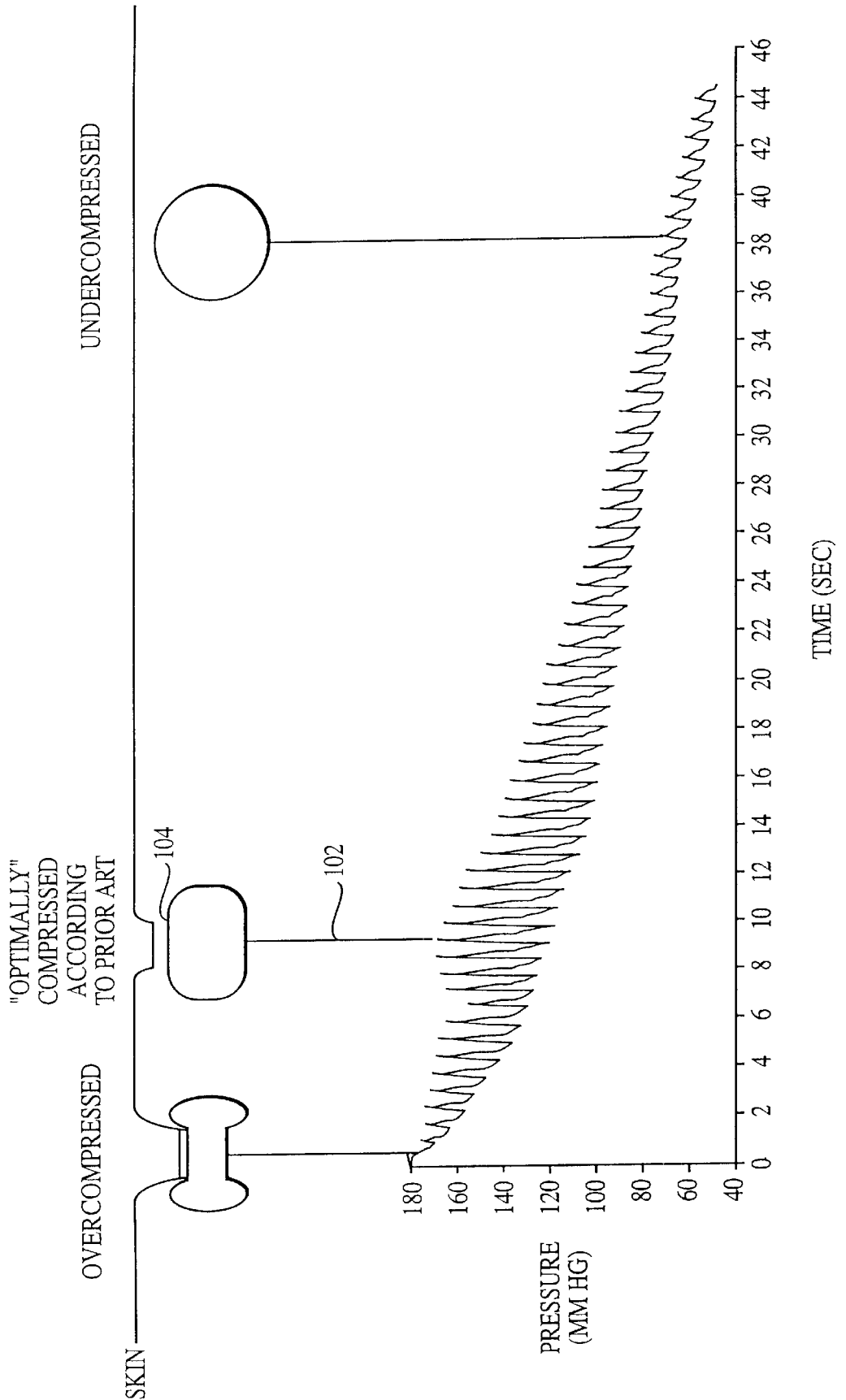
FIG. 1 is a composite graph illustrating the cross-sectional shape of an artery as a function of applied pressure and time according to the prior art "maximum pulsatile" theory.
Figure 2:
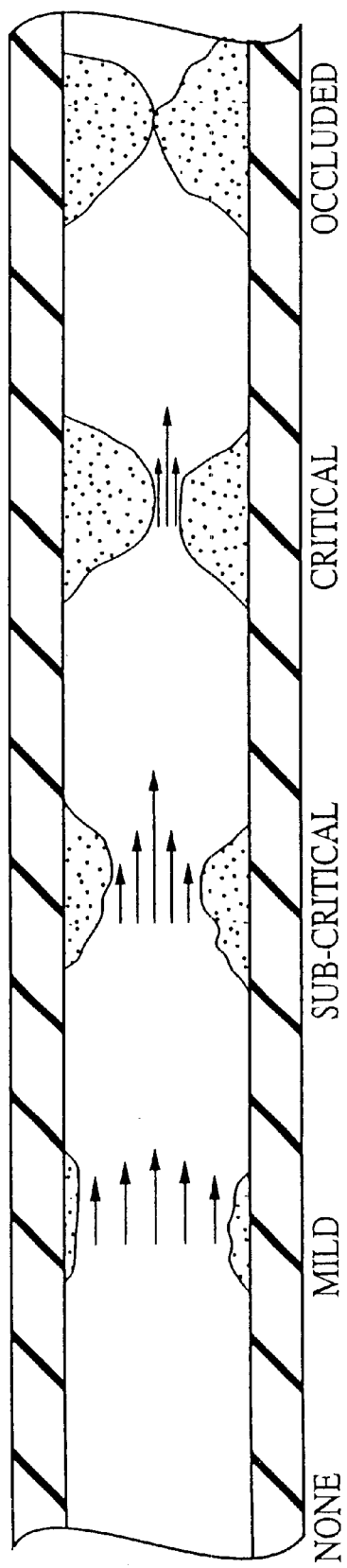
FIG. 2 illustrates a blood vessel with varying levels of stenosis formed on the walls thereof.
Figure 3:
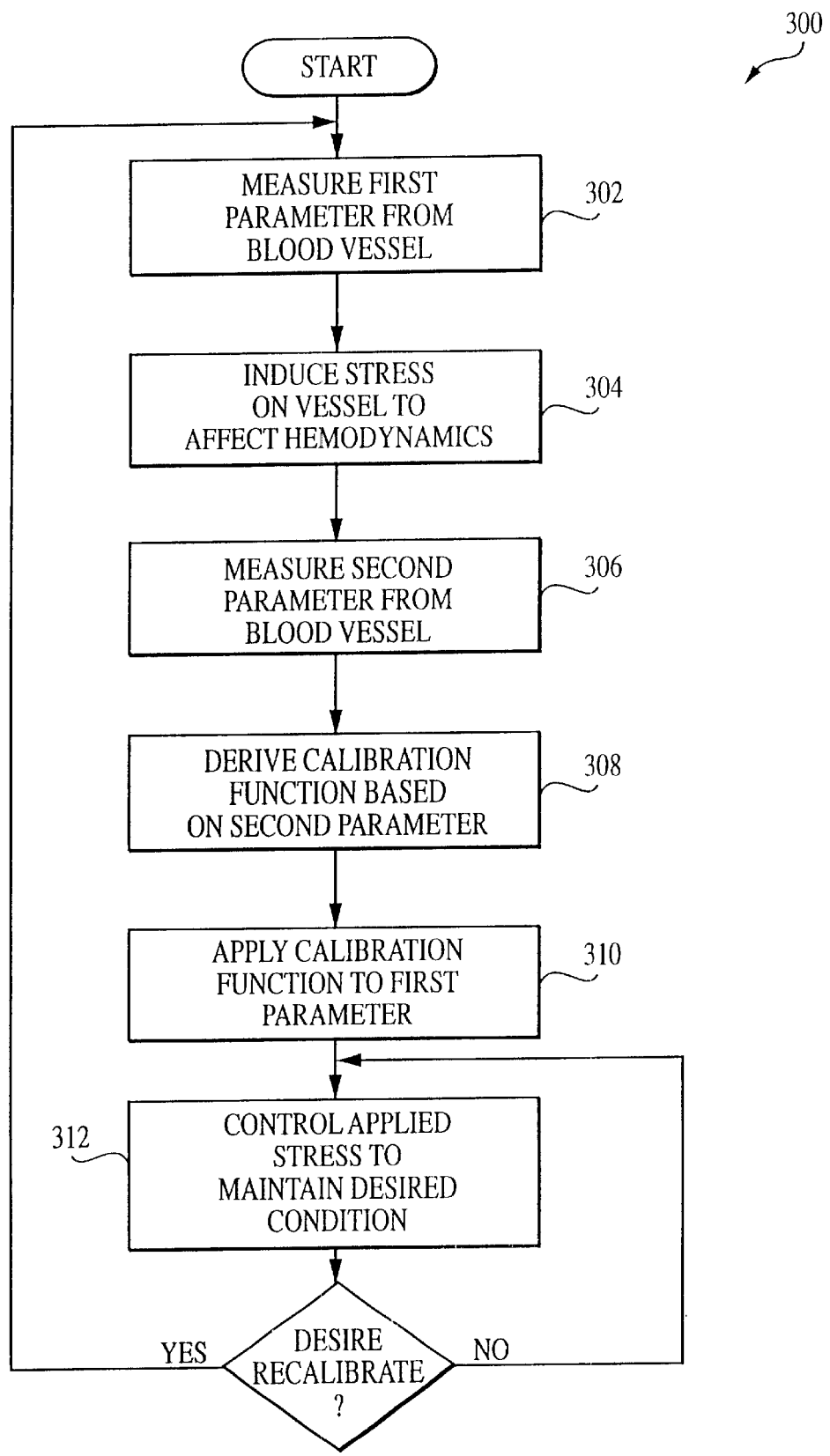
FIGS. 3–3e are a logical flow diagrams illustrating one exemplary embodiment of the method of assessing hemodynamic parameters within the circulatory system of a living subject according to the invention.

Referring now to FIG. 3, the method of assessing hemodynamic properties including blood pressure within the circulatory system according to the invention is described. As shown in FIG. 3, the first step 302 of the method 300 comprises measuring a first parameter from the blood vessel of a subject. In the present context, the parameter measured will be a blood pressure waveform derived from a pressure sensor or transducer disposed in proximity to the radial artery of the subject, as described in greater detail with respect to FIG. 3a herein. It will be recognized, however, that other hemodynamic parameters may be measured as previously noted. Implicit in the measurement of the first parameter is the existence of one or more error sources; i.e., the measured value of the parameter is not wholly representative of, or differs from, the actual value of the parameter existing in the circulatory system of the subject. In the instance of arterial blood pressure, the actual value is that existing within the artery itself, as may be measured by the A-line or "gold standard" technique of invasive arterial catheterization. Reasons for such errors or differences are discussed in more detail below with reference to FIG. 3a.

Next, in step 304 of FIG. 3, a stress is induced on the blood vessel which alters its hemodynamic properties (at least locally), thereby inducing changes in other parameters associated with the vessel or circulatory system as a whole. As discussed with respect to FIG. 3b, this stress comprises in one embodiment applanating or variably compressing the blood vessel as a function of time, thereby inducing changes in, inter alia, the mass flow rate (Q), velocity (v) or velocity gradient, and kinetic energy (KE) of the blood in the region of the applanation. It is noted, however, that stressors other than the applanation stress previously described may be applied to the subject to affect similar or other hemodynamic properties, such as, for example, circumferential occlusion (as would occur with a cuff-like device) to affect arterial cross-sectional area, or the localized introduction of chemical substances into the subject to affect the compliance of the artery. Many such stressor/hemodynamic parameter combinations may be used consistent with the invention.

Next, in step 306, a second parameter associated with the blood vessel is measured in order to facilitate derivation of a calibration function in step 308 below. As discussed in greater detail with respect to FIG. 3c herein, the second parameter in one embodiment comprises total blood flow kinetic energy, since this parameter exhibits certain easily identified "artifacts" as a function of the application of the stressor in step 304. As used herein, the terms "artifact" and marker are used synonymously, and refer to any identifiable feature or relationship existing within a data set. Other parameters which exhibit the same or other artifacts may be used to derive the calibration function however, including, for example, maximum blood velocity, blood vessel cross-sectional area, and blood mass flow rate.

In step 308 of FIG. 3, a calibration metric or function is next derived based on the parametric information derived in step 306. Specifically, one or more artifacts or markers are identified within the parametric data, these artifacts indicating when certain relationships between the actual and measured values of the first parameter of step 302 above exist. As will be discussed with reference to FIG. 3d herein, one embodiment of the process of deriving a calibration function comprises measuring total blood flow kinetic energy within the region of the applied stressor (applanation), and identifying changes within the systolic and/or diastolic velocity profiles as a function of the applanation (correlated to percentage reduction of cross-sectional area of the blood vessel).

In step 310 of the method of FIG. 3, the calibration function derived in step 308 is applied to the measurement of the first parameter of step 302 to generate a corrected or calibrated measurement. Note that if the first parameter is measured continuously (or periodically) as a function of time, the correction function of step 308 may be continuously or periodically applied as appropriate, thereby generating a calibrated measurement of the first parameter in an ongoing or continuous fashion. However, due to a variety of different factors, both the actual "A-line" arterial pressure and the scale or magnitude of the required calibration function may vary as a function of time; hence, any "calibrated" measurement based on the previously calculated calibration function will be in error. In one alternative, the user may simply periodically recalibrate by reapplying the stressor (e.g., performing another applanation sweep), generating an updated correction function, and applying this to the measured value of the first parameter.

However, as is described in greater detail herein below, the present invention advantageously provides the ability to generate a calibration function at a first time $t_1$, and then monitor the second hemodynamic parameter (e.g., maximum velocity, kinetic energy, area, or flow) continuously for indications of variation of the measured parameter. This is accomplished in step 312 of the method 300 by controlling the external pressure applied to the artery so as to establish a predetermined relationship between true arterial and external pressure, as described further below.

In step 312, the pressure applied to the artery is controlled to selected value of the first parameter so as to maintain the pressure across the artery wall (i.e., "transmural pressure") within the artery at or near a desired value. This process is referred to herein as "servoing" to a particular value. As discussed in detail with reference to FIGS. 5a–5d herein, this servoing generates a particular blood flow kinetic energy in the area of the applanation; changes in this kinetic energy are then used to identify changes in the true arterial pressure. This "continuous calibration" is a desirable attribute of the present invention, since the continued, accurate measurement of hemodynamic parameters with the blood vessel of a subject is of critical importance, especially in the context of surgery or other such life-threatening evolutions where arterial blood pressure is used as the basis for moment-to-moment decisions on treatment of the subject.

Figure 3A:
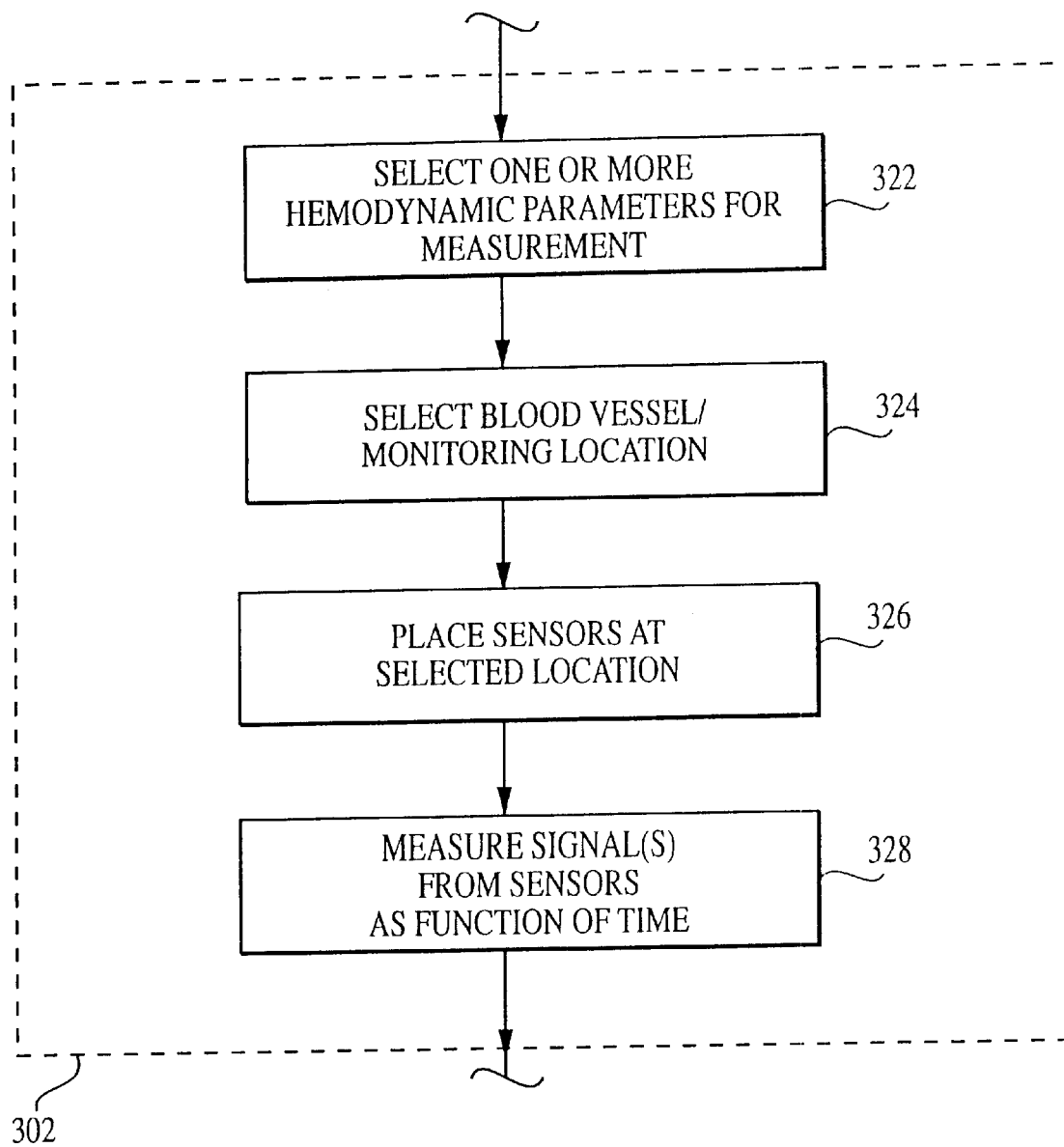

Referring now to FIG. 3a, one embodiment of the method of measuring one or more hemodynamic parameters within a living subject (step 302 of FIG. 3) is described. The first step 322 of the method 320 of FIG. 3a comprises selecting one or more hemodynamic parameters for measurement. Selection of the parameter(s) to be measured is a function not only of the condition to be assessed, such as the subject's blood pressure or severity of stenosis with an artery, but also on the monitoring location selected in step 324 below (i.e., certain parameters may only be measured at certain locations due to physical or other limitations, as in the case of a localized stenosis within an artery which is physically located at a discrete point).

Next, in step 324, a blood vessel within the body of the subject is selected for monitoring. Due to its accessibility and relative proximity to the surface of the skin, the radial artery of the human being is an excellent location for monitoring hemodynamic parameters within the circulatory system, although it will be appreciated that other locations on the human being (or other species) may be used for this purpose. As noted above, the location of monitoring also may be related to or determined by the type of condition to be assessed or monitoring to be performed. Of course, multiple monitoring locations may be employed, whether sequentially or in parallel, with the methods of the present invention.

With respect to the radial artery of the human being, it is further noted that anecdotal evidence suggests that the radial artery is only minimally affected by arterial diseases, including stenosis and calcification due to diabetes. The reasons for this observed behavior are beyond the scope of this discussion; however, this behavior is of some significance to the discussion of applanation stress provided herein with respect to FIG. 3b, since the presence of pre-existing arterial disease such as medial calcification could impact the ability to accurately measure arterial blood pressure. By selecting the radial artery when performing blood pressure measurements, which utilize controlled applanation as the applied stress, the user is effectively insulated from many potential error sources relating to pre-existing stenosis or calcification.

Next, in step 326 of FIG. 3a, one or more parametric sensors capable of measuring or sensing the selected parameter(s) is/are disposed in proximity to the selected blood vessel. In the case of measuring blood pressure on the radial artery of the human, a pressure sensor (transducer) is disposed physically in contact with the skin on the interior surface of the wrist, so as to be atop the radial artery. The transducer may be one of the well understood piezoelectric type, or any other type capable of producing a pressure signal in a known relation to the pressure applied to the surface thereof. Methods and apparatus for positioning the transducer(s) such that optimal signal coupling and sensing are achieved are also well known in the blood pressure measuring arts, and accordingly will not be described further herein. Note that while in contact with the skin of the wrist, the transducer(s) are initially maintained in a state of low or zero compression of the underlying tissue/artery, for reasons to be more fully explained herein.

In step 328, a signal is measured from the transducer(s) as a function of time. The signal may be measured discretely (e.g., at a predetermined interval) or continuously, depending on the desired frequency of monitoring. In the case of the exemplary pressure transducer previously described, the output signal for a continuous measurement will comprise a time variant waveform. In the case of arterial blood pressure, the waveform will generally track the actual "gold standard" arterial pressure, yet will include error or offset which varies with the pressure changes according to the various phases of the cardiac cycle. This time variant, non-linear error, or "variable error" between the measured and actual pressure waveform presents an additional complexity in the measurement process, one which the present invention is particularly well adapted to overcome as will be described in greater detail below.

Figure 3B:
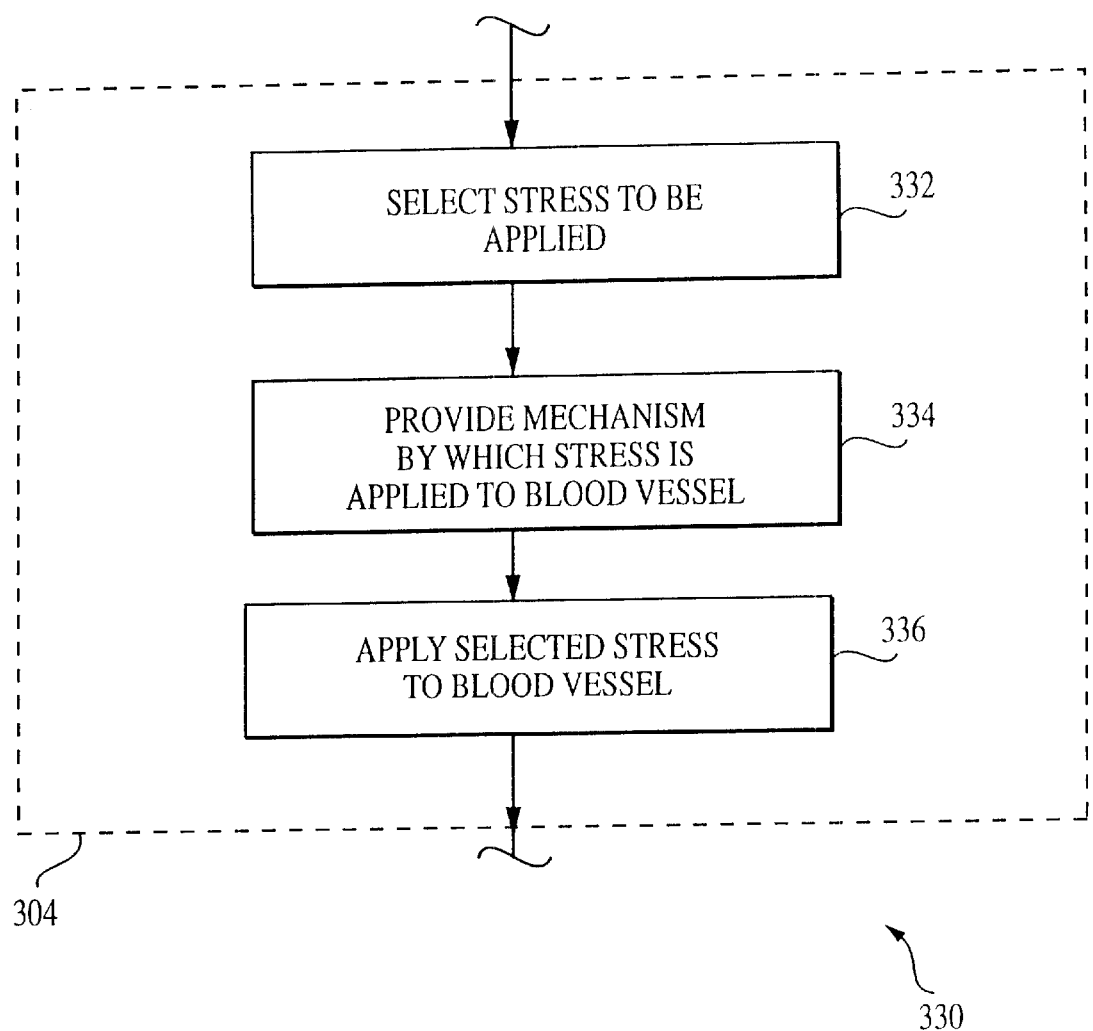

Referring now to FIG. 3b, one embodiment of the method of inducing one or more stresses on the circulatory system of the subject (step 304 of FIG. 3) is described in detail. In the first step 332 of the method 330, a stress to be applied is selected. As used herein, the term "stress" (or "stressor") refers to any physical or physiological change within the circulatory system of the subject which is artificially induced. In the present embodiment, the stress to be applied comprises applanation, or physical compression of the selected (radial) artery as a function of time. An applanation "sweep", as used herein, generally refers to the steady application of increasing or decreasing pressure to the artery in a direction generally normal to the surface of the skin overlying the artery. The concept of applanation is simply illustrated by one placing one wrist between the thumb and forefinger of the other hand, thumb atop the interior portion of the wrist, and slowly increasing pressure on the radial artery until the artery is occluded. It will be recognized, however, that as a general proposition, applanation as used herein may take on any variety of different forms, such as (i) a continuous linear rate of increasing or decreasing compression over time; (ii) a continuous non-linear (e.g., logarithmic) increasing or decreasing compression over time; (iii) a non-continuous or piece-wise continuous linear or non-linear compression; (iv) alternating compression and relaxation; (vi) sinusoidal or triangular waves functions; or (vi) random motion (such as a "random walk"). All such forms are considered to be encompassed by the term "applanation."

Figure 4A:
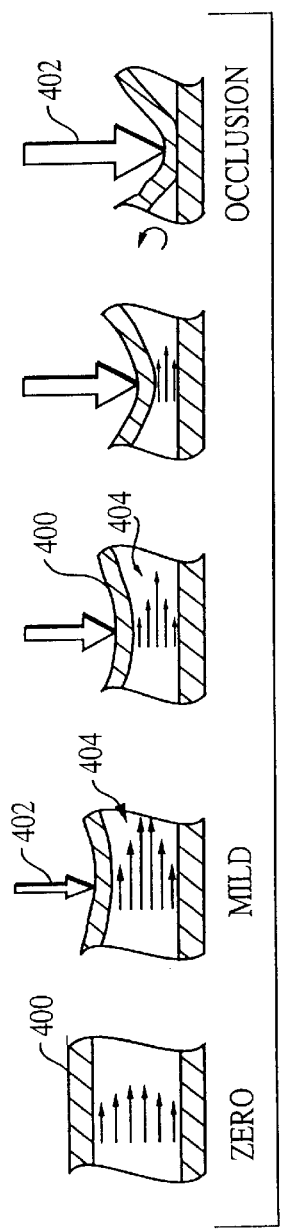
FIGS. 4a and 4b are graphs illustrating the relationship between blood velocity and reduction of the effective cross-sectional flow area of a blood vessel.
Figure 4B:
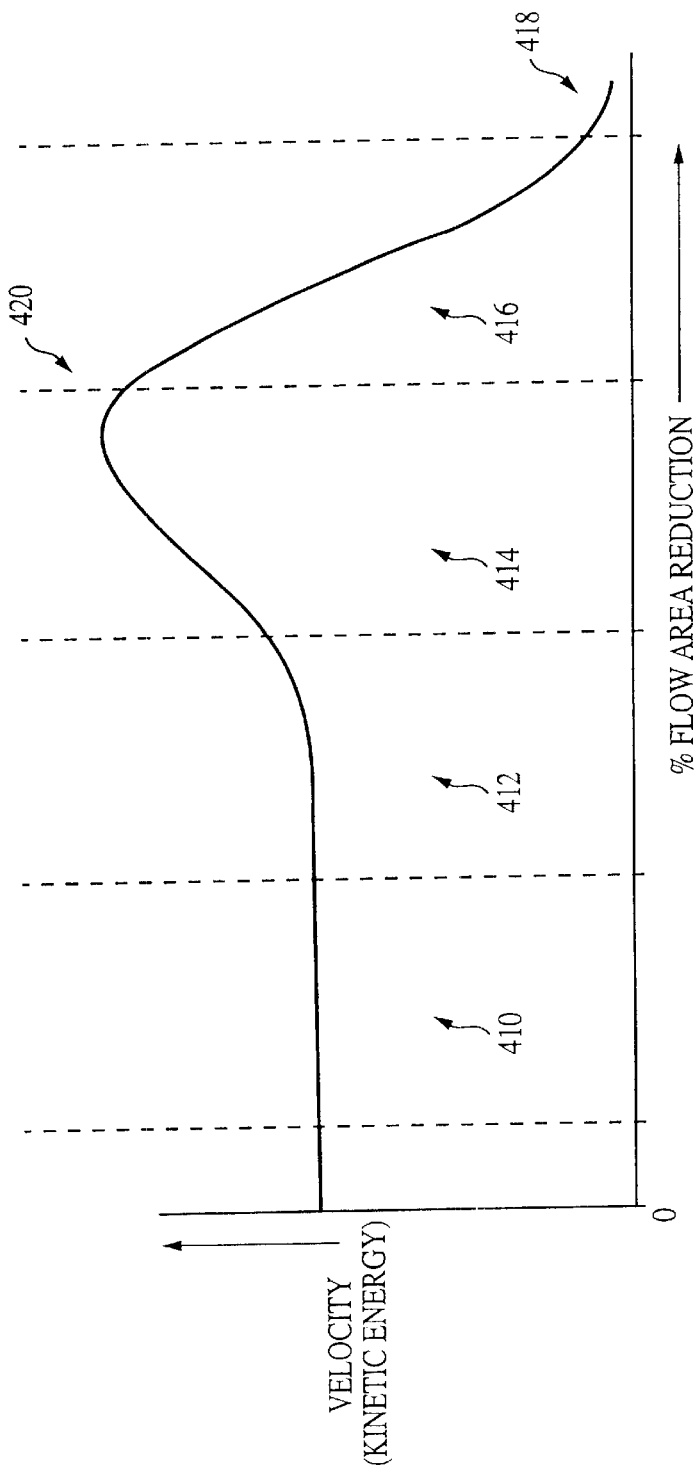

Referring to FIGS. 4a and 4b, the hemodynamic effects of applanation are described in detail. As will be readily recognized, the increasing applanation of an artery 400 such as the radial artery of the human results in a reduction in the effective cross-section of the artery. Similar to the arterial stenosis previously described, the applanation 402 reduces the flow area within the artery, thereby resulting in increased blood velocity (v) through the restriction to maintain a constant volumetric flow. This relationship is well understood in the fluid dynamics art. The profile of velocity across the reducing flow area is altered as well, as illustrated by the velocity gradient 404 of FIG. 4a. Hence, a higher maximum velocity, a higher velocity gradient, and a greater energy or pressure gradient across the restricted flow area result from applanation.

FIG. 4b illustrates the peak or maximum flow velocity within the artery as a function of percent reduction of the flow area of the artery. Total blood flow kinetic energy is similarly related to area due in part to its relationship to velocity, albeit somewhat more difficult to derive as described in greater detail below. Note that for the purposes of simplicity in the present discussion, the percent reduction of flow area is assumed to be directly proportional to the applanation pressure applied at the tissue (skin) surface, although in reality this relationship is substantially more complex as described further below. Further, FIG. 4b is generally illustrative of "steady state" operation, and does not examine the effects of variation in pressure due to, for example, the normal cardiac cycle, also discussed in greater detail below.

As illustrated in FIG. 4b, in the region of low applanation pressure 410, the percentage reduction of the flow area is small, and the effects on flow velocity and gradient are minimal. Volumetric blood flow (Q) is unaffected. As applanation pressure increases (region 412), the flow area is further reduced, and while the volumetric flow is maintained, the blood velocity, velocity gradient, pressure gradient, and kinetic energy begin to increase correspondingly. As applanation pressure further increases, the flow area is substantially reduced, and velocity, velocity gradient, pressure gradient, and kinetic energy increase substantially, while still maintaining volumetric flow under normal metabolic demand. In the stenotic artery, this region 414 corresponds to "subcritical" stenosis, i.e., the level of stenosis where the subject's excess volumetric capacity is significantly reduced, generally with few or no attendant symptoms. The appellation of "sub-critical" refers to the fact that the patient is asymptomatic with adequate tissue perfusion under normal metabolic demand, and only becomes symptomatic when the demand increases as occurs with exercise.

A further reductions in flow area produces a transition through what is known as the "critical" region 416; in the critical region, the flow area is so reduced so that there is inadequate energy to overcome the increased flow resistance, and volumetric flow is no longer maintained. Between these regions 414, 416, a velocity "peak" 420 is formed. Anecdotal evidence suggests that this peak 420 occurs roughly at point of 50% reduction in arterial diameter (corresponding roughly to 75% reduction in flow area). As a result, the blood velocity and the volumetric flow, and the flow kinetic energy distal to the stenosed area drop precipitously with further reduction in flow area. As the artery becomes fully occluded and flow area approaches zero (region 418), the volumetric flow Q approaches zero, as does blood velocity and flow kinetic energy.

Examination of FIG. 4b yields important information in terms of characterizing one response of the circulatory system to one applied stress. Specifically, the behavior of velocity as a function of applanation, and most notably the increase in maximum velocity within the velocity profile, allow the identification of the point where the pressure within the artery is effectively equal to that applied to the wall of the artery via external applanation. This condition is referred to herein as a condition of "zero transmural pressure". During the applanation sweep illustrated in FIGS. 4a and 4b, a point is reached at which the external pressure applied to the exterior of the artery wall is just offset by the internal pressure within the artery. Until this point is reached, no significant reduction in flow area (and resulting attendant changes in velocity, velocity gradient, volumetric flow (Q), or kinetic energy as previously described) occurs. However, as the applied pressure exceeds the arterial internal pressure, the diameter and cross-sectional area of the artery begin to be reduced, and the maximum flow velocity and velocity gradient begin to increase (region 414 of FIG. 4b). This increase in maximum velocity (and kinetic energy) is used in the present embodiment as a "marker" of the point at which the transmural pressure is roughly equilibrated.

However, as previously discussed, the circulatory system is not a static system, but rather dynamic and subject to significant intra-arterial pressure fluctuations, both due to the normal cardiac cycle, as well as other factors such as respiration (discussed below). Hence, such pressure fluctuations must also be considered when measuring hemodynamic properties, particularly intra-arterial pressure.

Referring now to FIGS. 5a–5d, the response of the circulatory system under the aforementioned dynamic pressure fluctuations is described. FIG. 5a illustrates a normal sinus cardiac rhythm 500 for a human being. Within this sinus rhythm 500 are both systolic periods 502 and diastolic periods 504 corresponding to various ventricular functions within the heart, as is well understood in the medical arts. These effectively represent maxima and minima within the sinus rhythm 500, and for the intra-arterial pressure.

FIG. 5b illustrates the displacement of the arterial wall as a function of the aforementioned sinus rhythm 500 of FIG. 5a, and the external applanation pressure applied to the artery per FIG. 5c. Two opposed arterial walls 510, 512 are illustrated in FIG. 5b for sake of clarity, although they are effectively mirror images of one another in terms of pressure response. As is well known in the art, arterial walls are typically (in the healthy human) substantially compliant vessels having significant elasticity and resiliency. Hence, as pressure within the vessel is increased, the opposing walls 510, 512 of the artery tend to deflect outward increasing the diameter of the artery, much as a balloon under inflation. Similarly, as intra-arterial pressure is reduced, the resiliency of the artery walls reduces the diameter. It is well known that human arteries cyclically expand and contract to some degree during the normal cardiac cycle.

As shown in FIG. 5b, variations in blood pressure within the artery deflect the walls of the artery outward to a maximum diameter 516 corresponding to the systolic pressure 502, and allow the artery walls to collapse to a minimum diameter 518 corresponding to the diastolic pressure 504. As the applanation pressure applied to the exterior of the artery (FIG. 5c) increases, the previously described condition of zero transmural pressure is reached successively for both the systolic and diastolic pressures. Specifically, with increasing applanation pressure, zero transmural pressure at the diastolic (lower pressure) condition 520 is achieved first, followed by zero transmural pressure at the systolic (higher pressure) condition 522. Considering the diastolic condition 520 first, as applanation pressure is increased beyond the zero transmural pressure condition, the effective diameter (and flow area) of the artery begins to progressively decrease, resulting in the increase in flow gradient and peak blood velocity and kinetic energy as previously described. As applanation pressure increases well above the diastolic pressure, the artery completely collapses during the diastolic portion of the cardiac cycle at point 527. Similarly, with increasing applanation pressure, the diameter of the artery at the systolic condition 522 also begins to decrease, with similar results, until the artery is completely collapsed under both diastolic portions 527 and systolic portions 529 of the cardiac cycle. Based on the foregoing behavior, two curves may be constructed (FIG. 5d) relating the variation in maximum blood velocity and percent flow area reduction (applanation pressure), both for the diastolic condition 520 and the systolic condition 522. Note that the velocity "peak" 524 of the systolic condition 522 occurs at a higher level of applanation than the corresponding peak 526 for the diastolic condition 520, since greater external pressure must be applied to collapse the artery in the former as opposed to the latter. It is further noted that at pressures falling between the systolic and diastolic maxima and minima of FIG. 5a, a family of curves similar to those of FIG. 5d may be constructed, such a family of curves being useful in characterizing the behavior of the artery and associated hemodynamic parameters during the entire cardiac cycle.

As with the velocity curve of FIG. 4b, the curves of FIG. 5d are useful for marking the point during the applanation sweep at which zero transmural pressure is achieved, both during the diastolic and systolic portions of the cardiac cycle (or any portion there between). The utility and application of this information is described in detail with reference to FIGS. 3d–3e herein.

While the foregoing exemplary application of compressive or applanation stress is useful in the measurement of, inter alia, blood pressure within the selected artery, it will be recognized that other types of stresses may be applied to induce response within the circulatory system. Artifacts or "markers" associated with these stresses may be utilized in a fashion generally analogous to that for the applanation stress; i.e., by correlating the presence of the markers or known relationships with certain hemodynamic conditions within the circulatory system in general or blood vessel in particular. Hence, the method of FIG. 3b is in no way limited to the use of compressive stress.

Returning again to FIG. 3b, the second step 334 of the method 330 of applying stress to the selected blood vessel comprises providing a mechanism by which such stress can be applied. In the context of applanation as described above, there is particular utility in using the aforementioned pressure transducer (used to measure the pressure waveform) as the means by which the artery is applanated, since this arrangement permits the pressure measurement to be made precisely at the point of applanation. An applanation mechanism of this type is described herein with respect to FIG. 12. However, it will be appreciated that a separate pressure transducer and applanation mechanism, or even other configurations, may be used in conjunction with the present invention.

In step 336 of FIG. 3b, the provided mechanism is utilized to apply the stress to the selected artery. In the specific case of applanation, an applanation "sweep" as previously described is applied, such that the pressure transducer is asserted at continually increasing levels of pressure against the skin of the wrist, thereby compressing the underlying artery. As with the method 320 of FIG. 3a, optimal placement and orientation of the applanation device over the artery may be determined using any variety of well understood prior art techniques, and accordingly is not discussed further herein. It is noted, however, that the foregoing method 320 maybe utilized even with non-optimal transducer placement (e.g., by manual placement by the individual administering treatment), so long as the signal coupling in such cases is adequate.

Figure 3C:
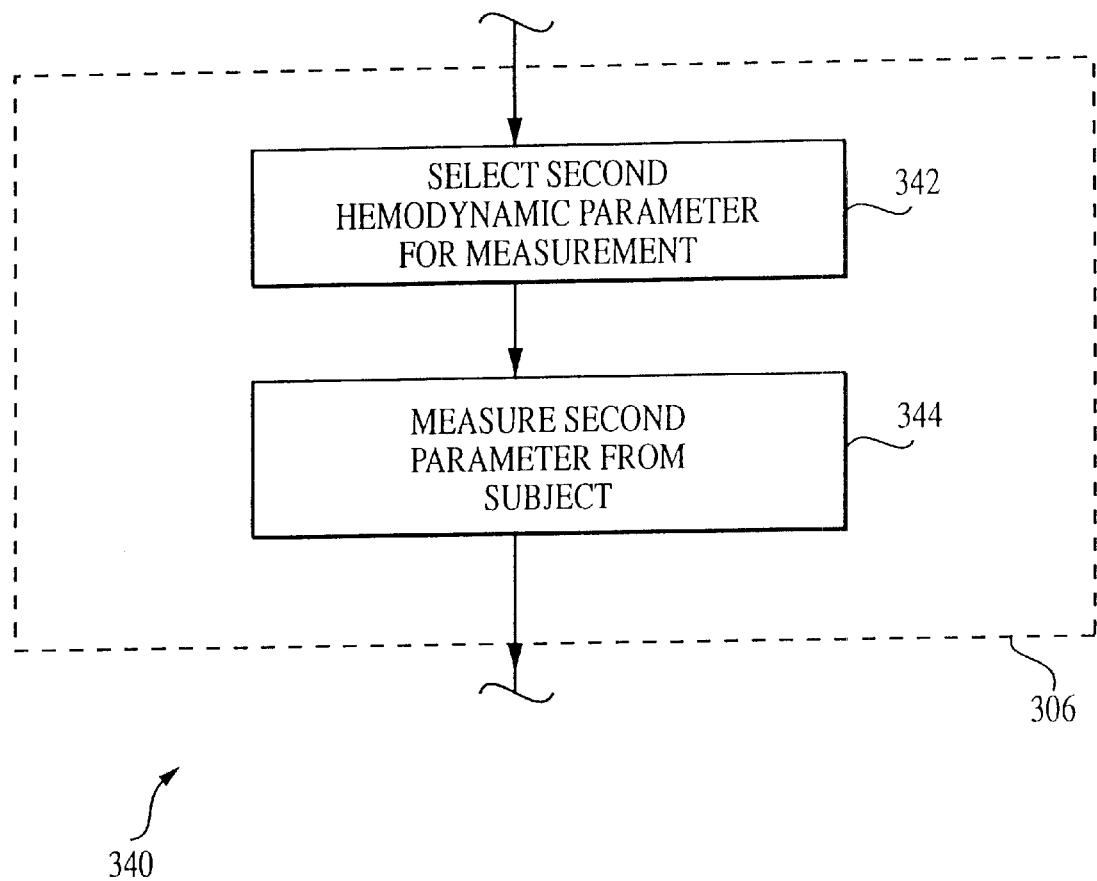

Referring now to FIG. 3c, one embodiment of the method of measuring a second hemodynamic parameter associated with the blood vessel (step 306 of FIG. 3) to facilitate derivation of a calibration function is described. In the first step 342 of the method 340, the second hemodynamic parameter to be measured is selected. Election of this parameter is in some respects coupled to the selection of the first hemodynamic parameter to be measured (FIG. 3a), as well as the selection and application of stress on the circulatory system (FIG. 3b). In the context of blood pressure measurement and the use of compressive stress (applanation) as previously described, several "secondary" hemodynamic parameters may conceivably be used to generate a calibration function, including, without limitation, blood velocity, total blood flow kinetic energy, and blood volumetric flow rate, as well as any variations or combinations thereof. Total blood flow kinetic energy is one particularly useful parameter to measure, as it contains one or more readily observable markers of the zero transmural pressure condition or other useful relationships. The total flow kinetic energy is also less prone to errors than certain other parameters, since it utilizes velocity information obtained across the whole blood vessel, as well as the amplitude information. Additionally, the peaking in the kinetic energy is more dramatic than the peaking in other parameters such as maximum velocity.

Next, in step 344, the selected "secondary" parameter is measured using an appropriate sensor or measurement technique. In the case of kinetic energy or blood velocity measurements, several well known techniques exist to generally measure these parameters non-invasively. Of particular note is the use of acoustic energy (e.g., ultrasound) to measure blood velocity. Specifically, acoustic measurement techniques generally employ the well known Doppler principle in measuring velocity, wherein the frequency shift associated with echoes reflected by the blood flowing within the blood vessel is analyzed to provide a measurement of blood velocity. Numerous different variants of acoustic blood velocity measurement techniques exist, including the use of a continuous acoustic wave (CW), and acoustic pulses (pulsed Doppler). Such techniques are well known and understood, and accordingly will not be described further here.

Similarly, acoustic measurement techniques may be used to derive a measurement of the kinetic energy of the blood flowing within the subject blood vessel. It is noted that as a result of the complex blood velocity gradient created with in the blood vessel during applanation (FIG. 4a), calculation of the kinetic energy of the blood within the blood vessel as a whole is not simply proportional to the square of the maximum blood velocity described above; rather, estimation of the kinetic energy requires the application of summation or integration techniques which capture the complexity of this gradient. Such summation/integration techniques for calculating blood kinetic energy are well known in the art, and accordingly are not described further herein.

In another embodiment, the applanation (external) pressure at which the desired marker is exhibited may be determined using time-frequency methodology as described in Applicant's co-pending U.S. patent application, Ser. No. 09/342,549, entitled "Method And Apparatus For The Non-invasive Determination Of Arterial Blood Pressure" filed Jun. 29, 1999, and incorporated herein by reference in its entirety. Using this time-frequency methodology, the applanation pressure at which the transmural pressure equals zero can be determined by constructing time-frequency representations of the acoustic energy reflected within the artery. When the time-frequency distribution is maximized, the zero transmural pressure condition is achieved. Hence, the maximal time-frequency distribution acts as yet another marker for the purposes of the present invention.

In yet another embodiment, the so-called acoustic "A-mode" may be used to monitor the second hemodynamic parameter. In this approach, acoustic waves are generated and transmitted into the blood vessel; reflections or echoes from the transmissions are received and analyzed to determine the relationship between the time of transmission and the time of receipt. Through such analysis, the relative diameter of the artery at different points in time, and different points within the cardiac cycle, can be determined. Analogous to the well known time domain reflectometer (TDR), the A-mode technique utilizes reflections generated by the transition of an acoustic wave across various boundaries between materials of different acoustic properties (e.g., the "near" artery wall/tissue boundary, the "near" artery wall/blood stream boundary, the blood stream/"far" artery wall boundary, etc.). Specifically, the relative timing of these reflections is analyzed to determine the distance between the various boundaries. Knowing the propagation speed of the acoustic wave through the different media, the distance between the reflective boundaries (i.e., tissue thickness, artery diameter, etc.) can be determined. Recalling that per FIG. 5b, the deflection of the artery walls (under both systolic and diastolic portions of the cardiac cycle) varies as a function of applanation pressure, changes in the arterial diameter (and area, related thereto) may be used as "markers" of the zero transmural pressure condition, or other conditions of significance, analogous to the use of increasing maximum velocity to identify such conditions. Specifically, when the diameter of the artery just begins to decrease, the externally applied pressure just slightly exceeds the internal arterial pressure at that point in time.

It will further be recognized that other acoustic modalities may be employed in conjunction with the invention described herein, including for "M-mode" (motion mode) or "B-mode" (brightness mode) both of which are well known in the acoustic signal arts.

Despite the use of acoustic waves in each of the foregoing embodiments for measuring the secondary hemodynamic parameter and markers associated therewith, it will be recognized that other non-acoustic techniques may be applied to identify such markers. For example, other methods of accurately measuring arterial diameter/area, such as using interferometry, may be employed to identify the zero transmural pressure condition. All such techniques are considered to fall within the scope of the present invention.

Figure 3D:
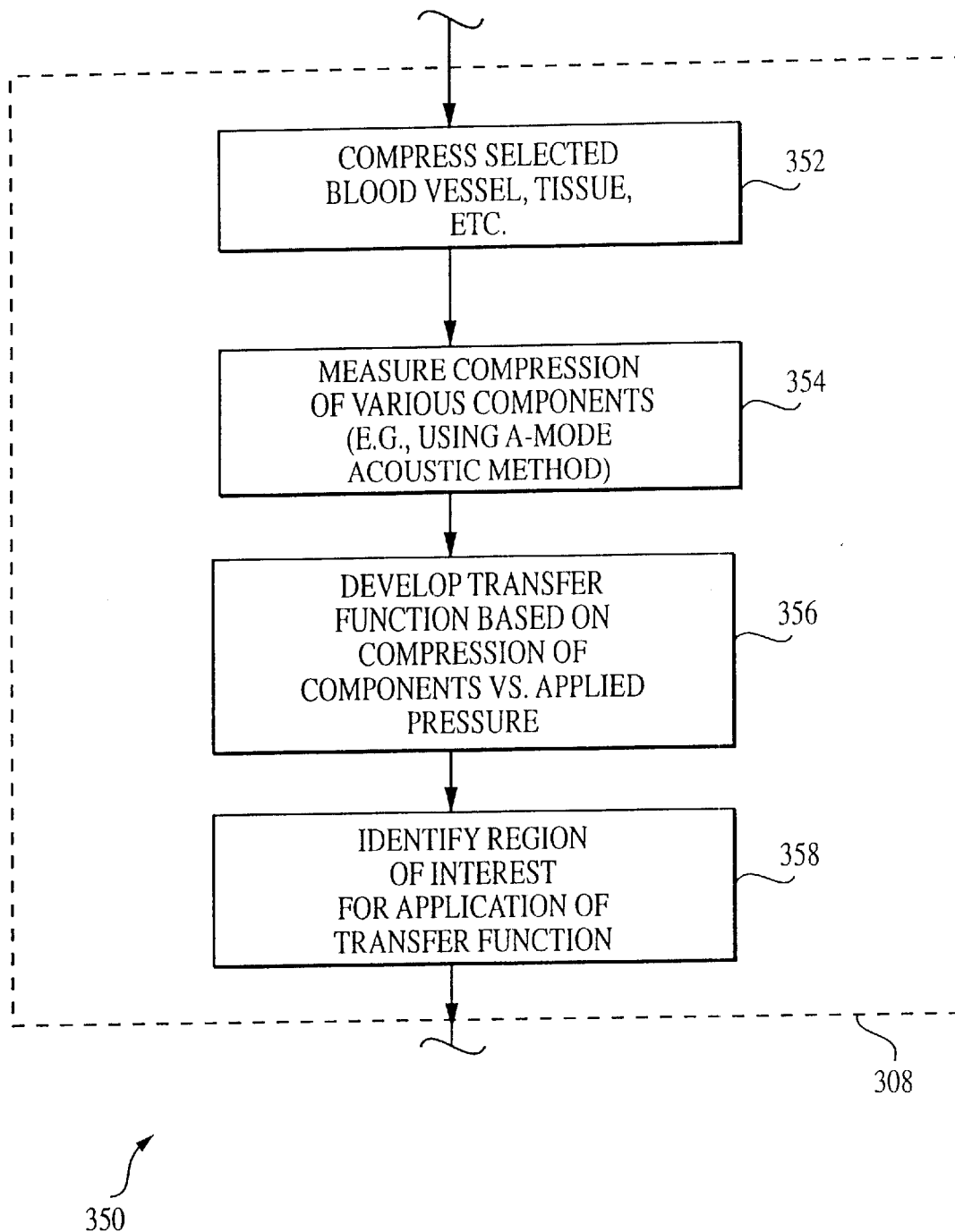

Referring now to FIG. 3d, the stressor magnitude at which the desired hemodynamic condition is achieved (e.g., applanation pressure at which zero transmural pressure is achieved) is correlated to the actual or true arterial pressure. In the simple case where there is a high degree of coupling between the applied stress and the stress actually felt by the blood vessel, the measured stress can be equated to the actual stress. Specifically, in the context of arterial blood pressure measurements where applanation (compressive) stress is applied, the pressure applied by the applanation device and sensed by the associated pressure transducer could be equated to the actual arterial pressure when the artifact or "marker" condition is observed. For example, if increasing blood kinetic energy correlates to a condition of zero or near-zero transmural pressure as previously discussed, the pressure applied against the artery wall when such increase in kinetic energy was observed would equate to true intra-arterial pressure. Hence, if the coupling between the point of pressure application (e.g., skin) and the artery wall was very high, the pressure applied at the point of application would approximate that applied to the artery wall, and therefore would also approximate the pressure within the artery.

However, as previously discussed, the tissue, tendons, and skin interposed between the artery wall and the pressure transducer in many cases create a complex relationship between the pressure applied by the transducer (or applanation mechanism) and the pressure actually felt by the artery wall. Simply stated, some of the pressure applied to the skin is used to compress this interposed material; hence, only a portion of the externally applied pressure is actually felt by the artery wall. Additionally, it is noted that tissue is also present below the blood vessel and above bone; some loss occurs in compressing this tissue as well.

Therefore, depending on the tissue compliance and degree of coupling for a given subject, a certain amount of error in the measurement of arterial pressure will be introduced when basing such a measurement on the externally applied pressure (e.g., that measured by the pressure transducer).

One prior art approach to this problem was to model the response of interposed material (for example, as a system of springs having linear force constants), and correct the pressure measured by the pressure transducer based on this model. This approach, however, is only as good as the model used; different subjects with different tissue thickness, density, and compliance values (as well as the location of the tendons and bone relative to each other and the artery) will respond differently, and these differences are not accounted for in such models. Furthermore, even for a single subject, changes in the response of the tissue and arteries of that subject may occur over time or as a function of externally induced stresses. For example, when an anesthetic is introduced into the circulatory system of the subject, a given artery may become substantially more compliant, thereby losing much of its resiliency. This change in compliance alters the relationship between actual and measured arterial pressure, and accordingly reduces the accuracy of any blood pressure estimate based thereon.

In contrast, the methodology of the present invention overcomes this significant limitation by measuring the actual response of the interposed tissue and material for each subject as opposed to generically modeling it as in the prior art. Specifically, the present invention generates a functional representation of tissue and arterial compliance based on actual compression of these components.

Figure 6:
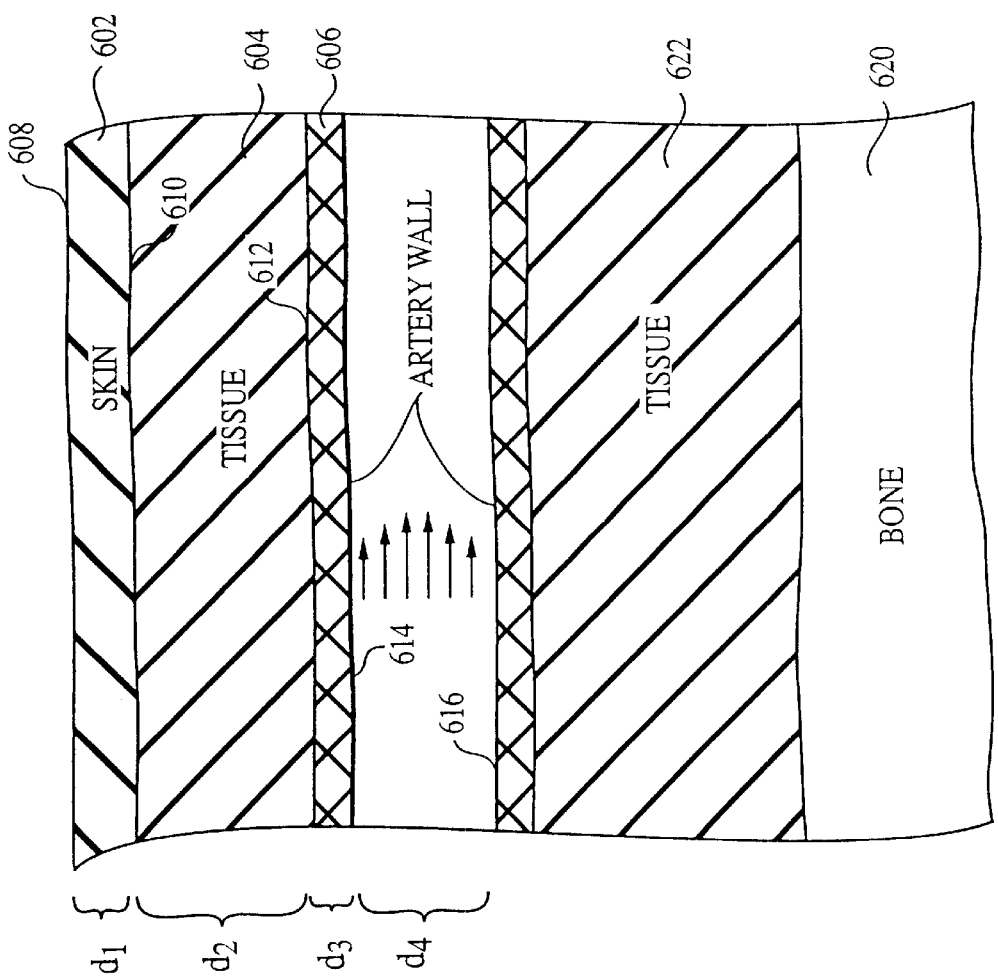
FIG. 6 is a cross-section of a portion of a typical human wrist illustrating the relationship between the artery, skin, and interposed tissue and bodily components.
Figures 7A, 7B:
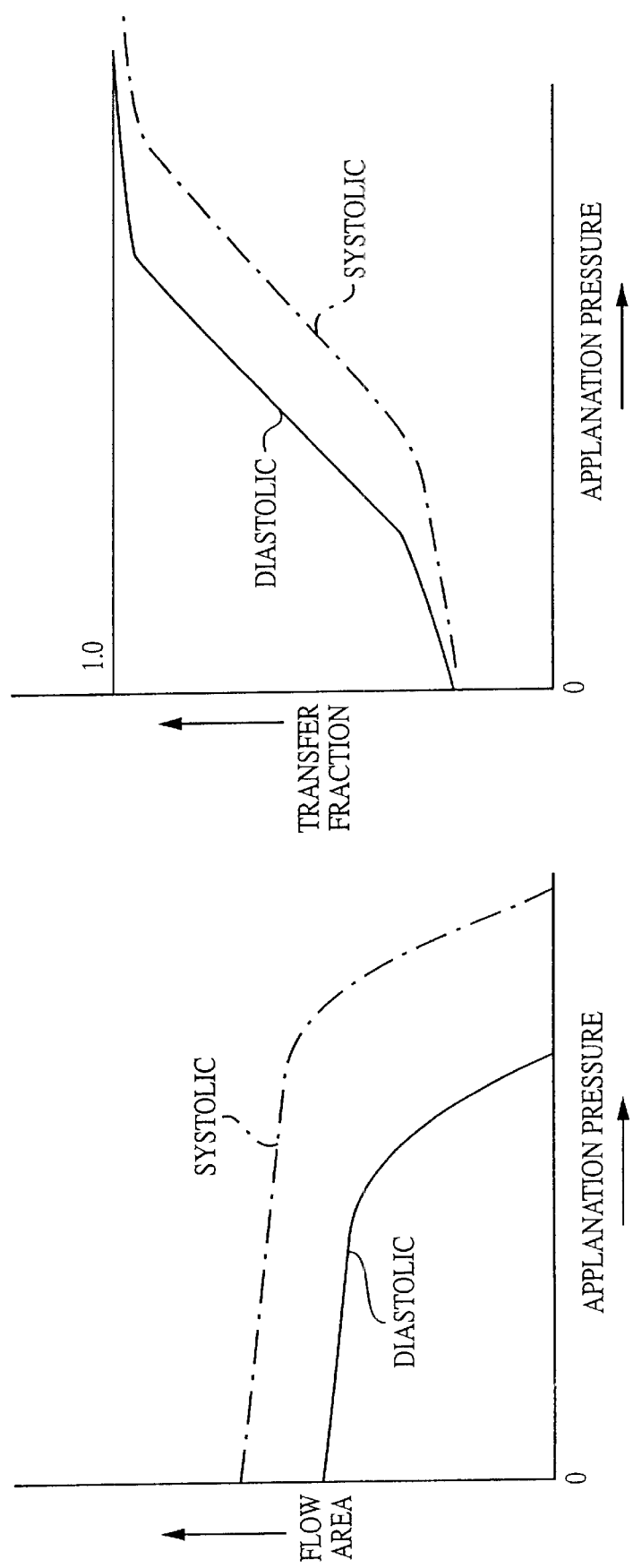
FIGS. 7a–7b are graphs illustrating an exemplary transfer function and transfer fraction, respectively, for the cross-section of FIG. 6, for both systolic and diastolic conditions.

In the exemplary embodiment of the method 350 illustrated in FIG. 3d, the aforementioned "A-mode" acoustic transmission is used to monitor the compression of each of the components interposed between the applanation device and the artery interior wall. The compression of these components (step 352) proceeds generally according to their individual material properties, which are unknown and interdependent and therefore exceedingly complex to model. However, by making direct observations of the actual compression of these components, the transfer function existing between the externally applied force and the force applied at the interface of the artery wall and the pressurized fluid (blood) within the artery can be approximately determined for each individual, and for the specific location being applanated. As illustrated in FIG. 6, the region between the interior wall of the artery and the surface of the skin above the artery may be divided into several discrete regions, such as the skin 602, tissue 604, and artery wall 606. The distances $d_1$, $d_2$, $d_3$ and $d_4$ between the surface of the skin 608 and the skin/tissue boundary 610, the skin/tissue boundary and the tissue/artery boundary 612, the tissue/artery boundary and the artery/blood boundary 614, and the artery/blood boundary 614 and the blood/artery boundary 616, respectively, are measured in step 354 using A-mode acoustic transmissions which identify reflections from these boundaries, as previously described. Additionally, the relative location of bone 620 and tendon (not shown) have great influence on the transfer loss. In effect, a restoring spring force of sorts exists between the tendon and tissue 622 and bone 620 and tissue 622. The loss of pressure transfer is at least partially associated with overcoming these restoring forces, as well as with the compliance of the tissue. Hence, during applanation (and during specific portions of the cardiac cycle), a transfer function between artery diameter (and flow area) and applied external pressure is developed per step 356. Specifically, for the diastolic and systolic portions of the cardiac cycle, different transfer functions will exist as illustrated in FIGS. 7a–7b. At low applied pressure (as measured relative to the actual intra-arterial pressure), relatively little compression of interposed tissue, underlying tissue/tendon, artery wall, etc. has occurred, and hence further increases in applied pressure generally contribute disproportionately to further compression of these components. At higher values of applied pressure, the interposed components are substantially compressed, and a relatively small fraction of any further increases in applanation pressure is used to compress the interposed and underlying components. Hence, in general, the "transfer fraction", or the ratio of transferred pressure to applied pressure, increases as a function of applied pressure, as illustrated in FIG. 7b. In the theoretical case of free-floating incompressible materials interposed between the pressurized blood in the artery and the transducer, the transfer fraction would be 1:1, indicating complete coupling.

The foregoing derived transfer function, can then be utilized to correct the error of the incomplete pressure transfer measured by the pressure sensing introduced by the interposed tissue, etc., by identifying the regions of interest per step 358. For example, if the zero transmural pressure condition within the artery during the diastolic portion of the cardiac cycle is achieved when a pressure of 60 mm Hg is measured, the true diastolic pressure will be some percentage higher, where the percentage is determined by the degree of pressure transfer loss. The transfer fraction for that monitoring location indicates the fraction or percentage of the intravascular pressure which is transferred to the surface of the pressure measuring sensor.

Note that the transfer function and/or transfer fractions may be represented and stored in any variety of different formats after measurement, such as in look-up tables in a digital random access memory as described further below with respect to the apparatus of FIG. 12. Furthermore, it will be readily appreciated that while the method 350 described above is used to determine the transfer fraction for one or more discrete pressure conditions (i.e., systolic and/or diastolic pressures), the transfer fraction may be readily determined for a range of pressures, thereby forming a transfer function as a function of pressure, as described in greater detail below. Hence, if the blood pressure of the subject does vary, the present invention utilizes this transfer function to correct the measured value of pressure within any pressure range.

Similarly, it will be recognized that methods of determining the transfer function/fraction other than the A-mode acoustic technique may be utilized, either alone or in conjunction with the A-mode technique.

Figure 8:
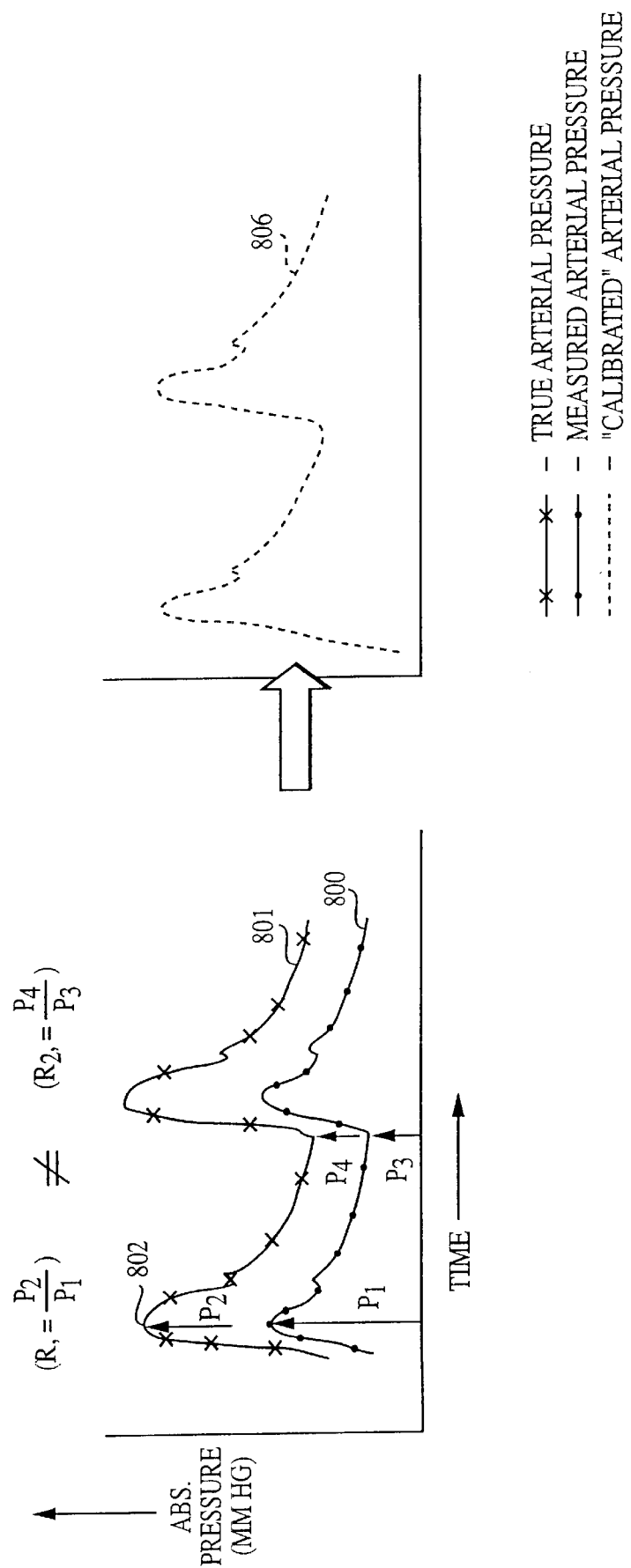
FIG. 8 is a graph of measured, actual, and scaled (calibrated) arterial pressure versus time for a typical human subject utilizing the invention.

In sum, the method 350 of FIG. 3d involves determining a transfer function/fraction as related to applied stress (e.g., pressure) for the subject and location being monitored, and calibrating the measured parameter at the designated "marker" point using the transfer function/fraction to determine the actual value of the parameter. In the case of blood pressure monitoring, this process involves applying an applanation pressure at which the kinetic energy term begins to increase (or alternatively, the maximum blood velocity begins to increase, the flow area begins to decrease, or some other desired condition is observed), and then correcting the measured value of the measured pressure using the transfer fraction to determine the actual intra-arterial pressure. When considered over the entire cardiac cycle, this method 350 produces a scaling or "stretching" function which is applied to the entire measured pressure waveform 800 to calibrate it to the true intra-arterial pressure 801, and thereby produce a "calibrated" waveform 806 as shown in FIG. 8. It is noted that depending on the portion of the measured pressure waveform being considered (e.g., diastolic portion, systolic portion, or there between), the ratio of actual or A-line intra-arterial pressure to the measured pressure will vary. This concept is graphically illustrated in FIG. 8, wherein the ratio of amplitudes at the systolic portion of the cardiac cycle $R_1$ 802 is not equal to the ratio of amplitudes at the diastolic portion $R_2$ 804.

It should be noted that while certain circumstances and individual subjects require the determination and application of a transfer function as described with respect to FIG. 3d, the general methodology of the invention may potentially be applied in some cases without a transfer function. For example, where a subject has a high degree of coupling between the skin and artery wall, the error associated with the pressure measured via the transducer placed at the skin surface may only constitute a small fraction of the total measurement, and would therefore be acceptable in certain monitoring environments. Hence, calculation and application of the transfer function is not a requirement of the present invention under all circumstances.

Figure 3E:
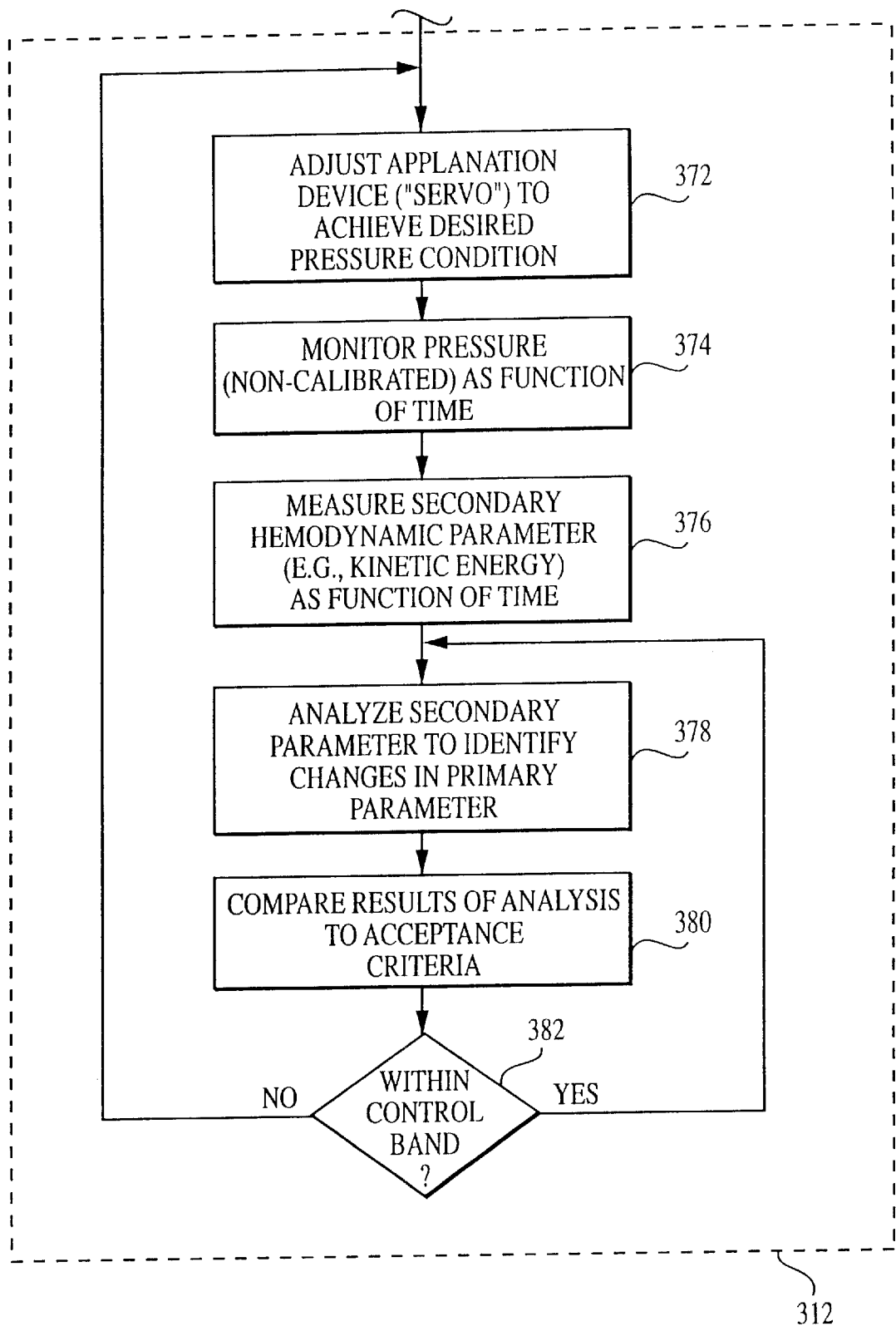

Referring now to FIG. 3e, the method of continuously calibrating the hemodynamic parameter being measured is described. As discussed with reference to FIG. 3d above, the transfer function is useful for correcting the measured pressure waveform for compression of the interposed tissue, artery wall, etc. This transfer function is obtained during an applanation sweep performed at a given monitoring location on the subject, such as the radial artery. However, to permit continuous monitoring of the subject's arterial blood pressure, a mechanism is needed whereby changes in the measured parameter can be accurately observed and scaled between calibration events (e.g., applanation sweeps).

As previously discussed, prior art calibration approaches relied on periodic calibration events (such as asculatory cuff measurements) to "continuously" calibrate the measured pressure waveform. The term "continuously" used with reference to these systems is somewhat of a misnomer, since what actually occurs is periodic (rather than continuous) updates of the scaling function. This approach presents at least one serious defect, that being the lack of calibration during the interval between periodic calibration updates. Depending on the activities of the subject being monitored, their true arterial blood pressure may vary significantly in a short period of time, and in some cases in a rapid or prompt fashion. For example, during surgery, actions by the surgeon such as artery re-section may have profound effects on the circulatory system of the subject, including their arterial blood pressure. Similarly, the difference between pre-induction (i.e., pre-anesthesia) and post-induction blood pressure values may be dramatically different, due in large part to the change of compliance within many of the arteries in the subject's body resulting from the anesthetic.

Since the prior art approaches in no way monitor the actual hemodynamic properties occurring within the artery, if such significant changes in true arterial blood pressure occur between periodic calibration events, they in many cases will go undetected. Rather, such prior art approaches typically monitor blood pressure tonometrically, these measurements being potentially very different from true arterial pressure. The prior art systems typically adjust the scaling factor or calibration to account for the measured change in tonometric blood pressure (which may or may not be close to true blood pressure). The result of this method is to produce so-called "calibrated" blood pressure values which in fact are not calibrated, but comprise a widely varying scaling component. This failure to track actual or true arterial blood pressure between calibration events can be catastrophic in cases where minute-to-minute measurements of blood pressure may be critical, such as during surgery.

The methodology of the present invention overcomes the foregoing significant limitations of the prior art by using the measured "secondary" hemodynamic parameter previously described to track changes in the first or "primary" measured hemodynamic parameter (e.g., blood pressure), as described in detail below.

In one embodiment, the kinetic energy of the blood is monitored using the aforementioned acoustic (or other) techniques while the zero transmural pressure state (or some other state determined to be of significance) is maintained within the artery, as illustrated by the method 370 of FIG. 3e.

Specifically, the applanation device, which in the embodiment described below with respect.to FIG. 12 also comprises the pressure and ultrasonic transducers, is "servoed" or continually modulated against the skin above the monitored artery in step 372 so as to maintain the desired pressure condition. The measured (non-calibrated) primary parameter, here pressure, is monitored as a function of time at the same time per step 374. Depending on the particular application, the modulation of step 372 may be controlled so as to maintain the transmural pressure at a specific value during the diastolic portion of the cardiac cycle, or alternatively during the systolic portion of the cycle. As yet another alternative, the applanation device may be modulated or servoed to maintain the mean transmural pressure (calculated over one or more complete cardiac cycles) at a predetermined value. Servoing may also be conducted to maintain a desired maximal blood velocity condition, or cross-sectional area condition. Many other such "target" servo values may be substituted with equal success, and the choice of such values, as well as the parametric relationship on which this value is based. (e.g., the region on the maximum velocity v. flow area plots of FIG. 5d in which it is desired to operate) is solely determined by the needs of the user and the particular application in which the method is employed.

Next, in step 376, the secondary hemodynamic parameter is measured as a function of time using a suitable technique. In the present embodiment, the total kinetic energy (or maximum blood velocity) is measured using an acoustic Doppler system of the type previously described.

In step 378, the value of the secondary parameter measured in step 376 is analyzed to identify changes in the primary parameter. For example, when the applanation device is servoed to maintain zero transmural pressure in the diastolic portion of the cardiac cycle, changes in kinetic energy are used to track changes in intra-arterial blood pressure. The results of this analysis are compared to predetermined acceptance or control criteria per step 380 to determine if further adjustment of the applanation device is required (step 382). For example, if significant increases or rates of increase in total blood flow kinetic energy were observed in steps 378–382 (thereby indicating that the applanation pressure felt by the artery wall was exceeding the true intra-arterial pressure), then the applanation pressure could be reduced so as to maintain the artery at a near-zero transmural pressure condition, as reflected by smaller increases or rates of increase in kinetic energy. It will be recognized that any type of control scheme which controls one parameter based on measurements of one or more other parameters may be used to effect the desired behavior, including fuzzy logic or PID controllers of the type well known in the control system arts.

Notwithstanding the foregoing, it will be recognized that the continuous calibration of the first hemodynamic parameter using the method of FIG. 3e may be accomplished using additional or other secondary parameters including, for example, maximal blood velocity and/or arterial cross-sectional (flow) area.

It is also again noted that in contrast to prior art approaches, the techniques of FIGS. 3–3e discussed above advantageously involve no modeling or estimation of parameters within the circulatory system of the subject being monitored; all information is derived via direct measurement of the subject at the selected monitoring location, and therefore is particularly adapted to that individual and that location.

Method of Characterizing Hemodynamic Response of Circulatory System

Figure 9:
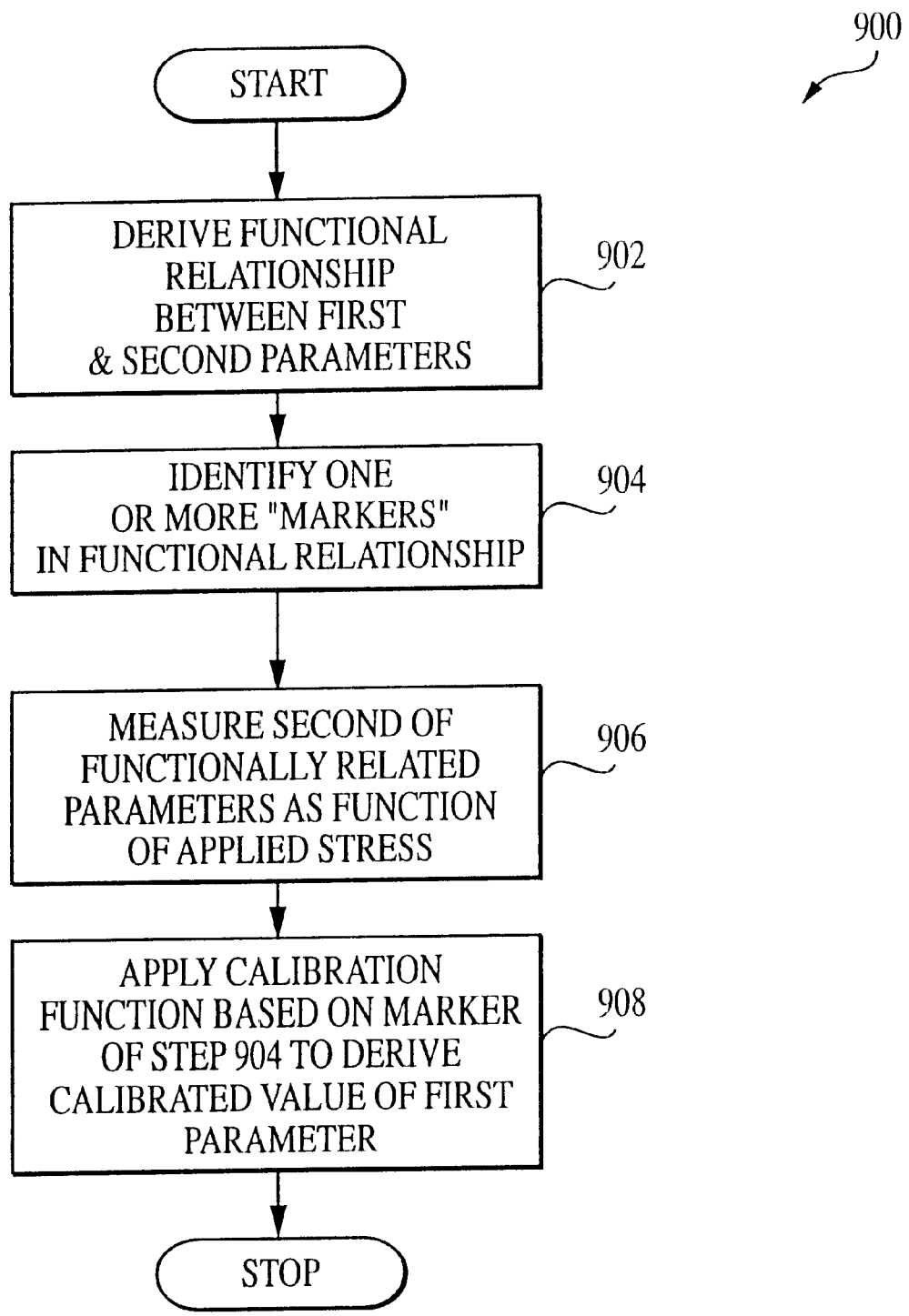
FIG. 9 is a logical flow diagram illustrating one exemplary embodiment of the method of modeling the hemodynamic response of the circulatory system of a living subject according to the invention.

Referring now to FIG. 9 a method of characterizing the hemodynamic response of the circulatory system of a living subject is disclosed. As illustrated in FIG. 9, the first step 902 of the method 900 comprises deriving a first functional relationship between first and second parameters associated with a blood vessel in relation to an applied stress. In the context of arterial blood pressure measurement, the first functional relationship derived in step 902 comprises the relationship(s) between arterial cross-sectional area (applanation pressure) and total blood flow kinetic energy as previously described herein, although it will be recognized that any number of different functional relationships may be substituted therefor. For example, the functional relationship between maximal blood velocity and flow area, velocity gradient and flow area, or volumetric blood flow (Q) and flow area, may be used if desired.

Next, in step 904, one or more artifacts or markers present within the functional relationship derived in step 902 above are identified. In the case of arterial blood pressure measurement as previously described, the artifact comprises the increasing kinetic energy or blood velocity after the condition of zero transmural pressure is achieved for the diastolic and/or systolic conditions. These artifacts comprise points for the calibration function previously described with respect to FIGS. 3c–3e herein. Alternatively, the points at which wall diameter begins to decrease at the systolic and diastolic portions of the cardiac cycle, as measured by A-mode ultrasound or other similar techniques, may constitute a marker of zero transmural pressure.

Next in step 906, one of the functionally related parameters from step 902 above is measured non-invasively as a function of the stress applied. In the above-referenced example, this measurement would comprise measuring blood velocity within the artery as a function of time (and applanation pressure), and deriving total flow kinetic energy therefrom.

Lastly, in step 908, the calibration "function" (which in theory may be as few as one data point) is applied to the measured response of a selected parameter associated with the circulatory system based on the artifact identified in step 904, thereby producing a calibrated characterization of the response of that parameter. For blood pressure, the selected parameter is tonometrically measured (i.e., non-calibrated) pressure, and the calibrated characterization comprises calibrated (or "true") arterial blood pressure determined at, inter alia, the point where the kinetic energy of the blood begins to increase.

Furthermore, the effects of potential errors (such as that due to incomplete signal transfer due to tissue compliance) may be accounted for as part of step 908 as well.

Method of Calibrating for Periodic Error Sources, Including Respiration

Figure 10:
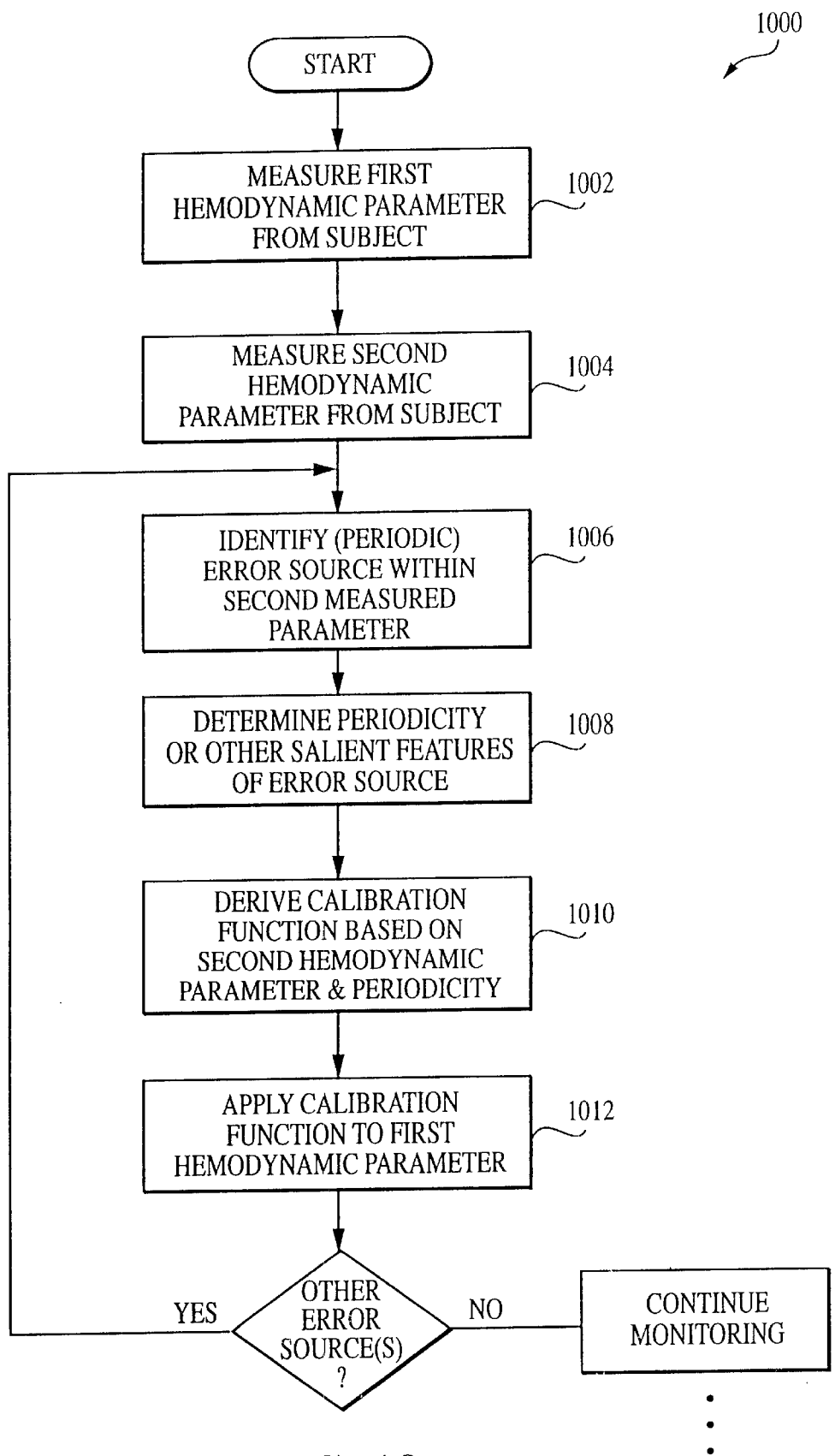
FIG. 10 is a logical flow diagram illustrating one exemplary embodiment of the method of calibrating a hemodynamic parametric measurement for respiration or other periodic error sources according to the invention.

Referring now to FIG. 10, a method of calibrating a hemodynamic parametric measurement for periodic error sources is disclosed. The first step 1002 of the method 1000 comprises measuring a first hemodynamic parameter associated with a blood vessel. As previously described, this parameter may comprise arterial blood pressure, or another parameter such as differential pressure, etc. In the case of arterial blood pressure, this parameter is the non-calibrated pressure waveform measured using the tonometric pressure transducer.

Next, in step 1004, a second hemodynamic parameter is measured on the subject, as previously described. This second hemodynamic parameter may comprise kinetic energy, maximum blood velocity, arterial diameter, flow area, etc. In one embodiment, the kinetic energy is calculated based on measurements of blood velocity made using Doppler ultrasound.

Figure 11:
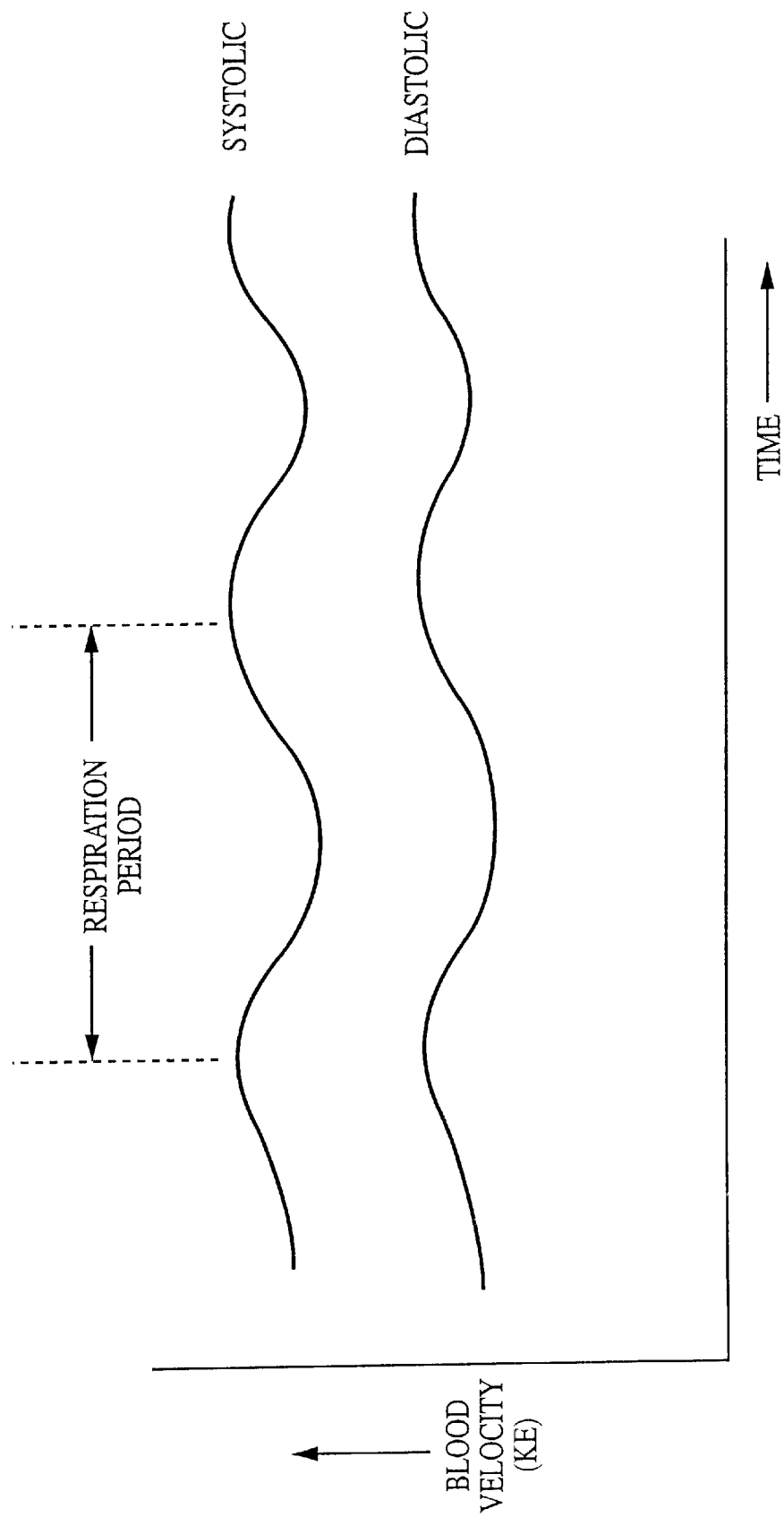
FIG. 11 is plot of the velocity and kinetic energy (KE) of blood flowing within a typical blood vessel, illustrating the effects of respiration thereon.

Next, in step 1006, periodic error sources associated with the first parameter are identified within the second parameter. In one exemplary case, the periodic error source relates to the respiration of the subject being monitored, illustrated in FIG. 11. As shown in FIG. 11, the velocity and kinetic energy of the blood flowing within the radial artery of a human being generally includes a time-variant, periodic component. This periodic behavior is due in substantial part to the respiration cycle of the subject, and occurs at much lower frequency than the typical cardiac cycle. Hence, the normal cardiac cycle 1102 can be thought to be "amplitude modulated" by the periodic respiratory variance 1104.

The origin of the respiratory periodic variance relates to the varying pressures which occurs as the diaphragm ascends and descends. With inspiration, the diaphragm should descend, increasing intra-abdominal pressure and decreasing intra-thoracic pressure. The increase in the pressure differential from the abdomen to the right atrium increases the volumetric flow back to the right atrium. With expiration, as the diaphragm ascends, the intra-abdominal pressure decreases and the intra-thoracic pressure increases. The result is more venous return to the abdomen from the lower extremities, but less return to the right atrium. The cyclical changes in volume and pressure are reflected everywhere throughout the circulatory system, since it is a closed system.

The aforementioned cyclical respiratory changes result in variant flow velocities and kinetic energies for, inter alia, the measured diastolic and systolic pressures. In a normal adult human being, anecdotal evidence obtained by the Applicant herein suggests that the magnitude of such variations may be on the order of 20 mm Hg or more in severe cases. Taken as a fraction or percentage of the systolic and diastolic pressures, this variation in pressure due to respiration may be significant, especially for the lower diastolic pressures measured when the subject is not ambulatory, such as during surgery.

These variations are accounted for in the present invention, when required, by synchronizing the derivation of the calibration function from the measurement of the secondary hemodynamic parameter (e.g., velocity, kinetic energy, or area). Specifically, in step 1008 of the method 1000, the periodicity of the respiratory variation is analyzed and determined, and this information is used to synchronize the derivation of the calibration function to a common point on the period ("carrier") respiration waveform. Identification of the respiratory component and its periodicity is accomplished using any one of a number of algorithms well known in the signal processing arts; accordingly, such algorithms will not be discussed further herein. It is noted that since the respiratory rate and/or "depth" of respiration of the subject may vary with time, thereby affecting the periodicity and magnitude of pressure/flow variations within the artery, the periodicity of the respiratory effect should be continually (or at least frequently) calculated.

Next, in step 1010, a calibration function is developed based on measurements of the secondary hemodynamic parameter taken at the periodicity prescribed by the result of step 1008. For example, a series of blood velocity measurements may be taken every 7 seconds (each measurement corresponding to the same relative point on the respiration waveform, but displaced in time), and this information used to derive kinetic energy values and a calibration or "stretching" function as described previously herein with reference to FIGS. 3–3e.

Lastly, in step 1012, the stretching function of step 1010 is applied to the measured (i.e., non-calibrated) waveform of step 1002. Note that by virtue of measuring the second hemodynamic parameter at a similar point relative to the respiration waveform, the effects of respiration across the entire respiration cycle are accounted for. Hence, the derived stretching function may be applied to the entire non-calibrated pressure waveform), as opposed to only those portions of the waveform corresponding to the points in time when the second parameter was actually measured. Assuming the pressure transfer to be relatively linear around the systolic pressure variations with respiration, and the diastolic pressure variations with respiration, no other correction would be necessary. An additional correction can be applied if the non-linearities are significant enough, by calculating the correction factors at a different phase of the respiration cycle. This represents a significant advantage in providing a continuously (as opposed to periodically) calibrated representation of true arterial blood pressure.

It will be appreciated that while the foregoing discussion is cast in terms of periodic error due to respiratory system effects, other types of errors, periodic or aperiodic, may be accounted for using the methodology of the present invention as illustrated in FIG. 10. For example, the effects of an arrhythmia within the heart of the subject may be identified and accounted for during derivation of the calibration function. An arrhythmia within the heart of the subject may be identified using signal processing algorithms specifically adapted for the purpose of identifying aperiodic components within waveforms, such algorithms being well known to those of ordinary skill in the signal processing arts. Numerous other. types on non-periodic error components may also be identified in conjunction with the method of FIG. 10.

Apparatus for Hemodynamic Assessment

Figure 12:
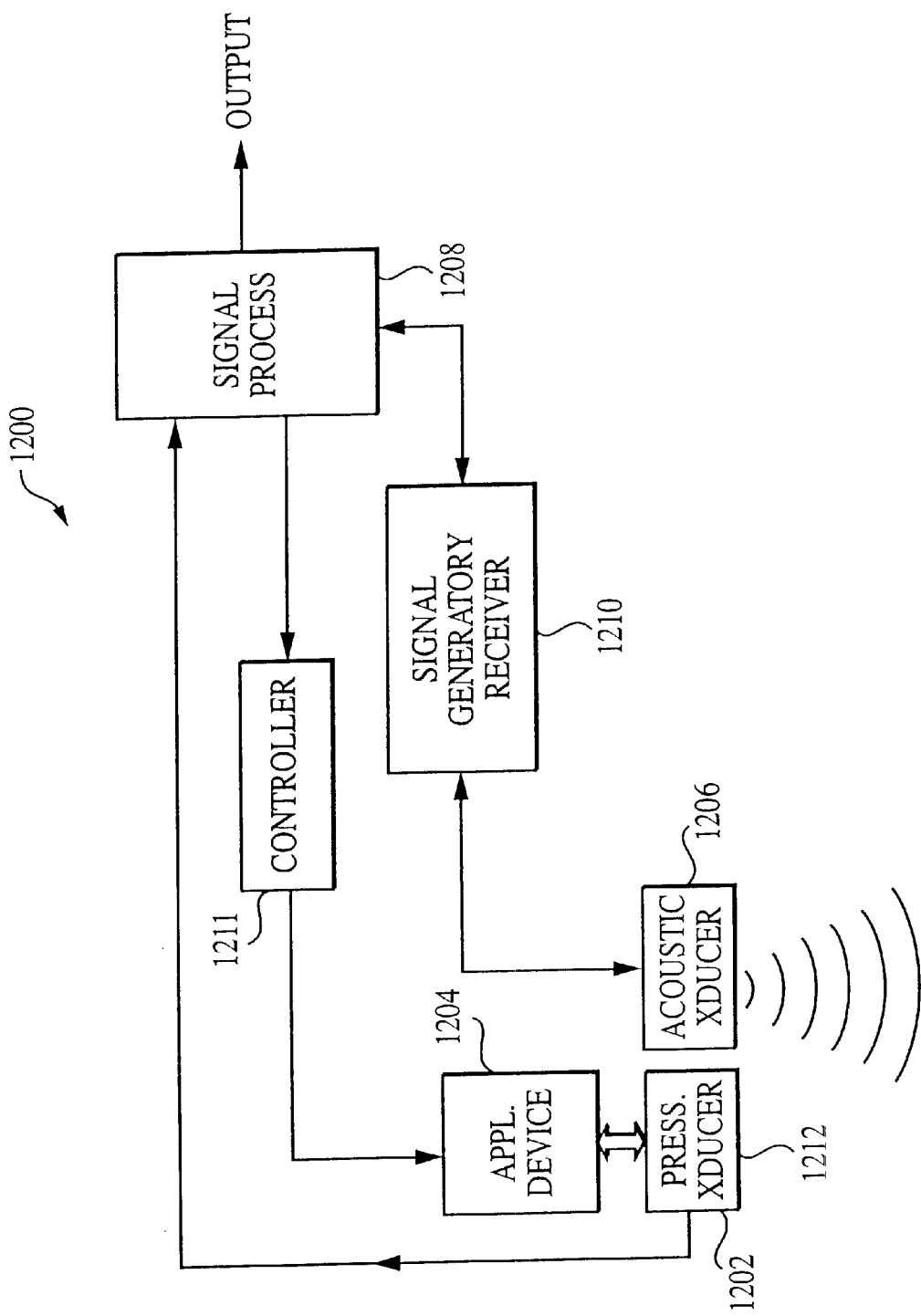
FIG. 12 is a block diagram of one exemplary embodiment of the apparatus for measuring hemodynamic properties within the blood vessel of a living subject according to the invention.

Referring now to FIG. 12, an apparatus for measuring hemodynamic properties within the blood vessel of a living subject is described. In the illustrated embodiment, the apparatus is adapted for the measurement of blood pressure within the radial artery of a human being, although it will be recognized that other hemodynamic parameters, monitoring sites, and even types of living organism may be utilized in conjunction with the invention in its broadest sense. The apparatus 1200 of FIG. 12 fundamentally comprises a pressure transducer 1202 for measuring blood pressure from the radial artery tonometrically; an applanation device 1204 coupled to the transducer 1202 for varying the degree of applanation (compression) on the artery; an acoustic transducer 1206 for generating acoustic emissions and reflections thereof, these acoustic emissions being used to derive blood velocity (and kinetic energy); a signal processor 1208 operatively connected to the pressure and acoustic transducers 1202, 1206 for analyzing the signals generated by these transducers and generating a calibration function based thereon; a signal generator/receiver 1210 used to generate acoustic signals for transmission into the artery, and receive signals from the acoustic transducer 1206; and a controller 1211 operatively coupled to the applanation device 1204 and the signal processor 1208 for controlling the degree of applanation pressure applied to the artery.

The pressure transducer 1202 is, in the present embodiment, a piezoelectric transducer clement which generates an electrical signal in functional relationship (e.g., proportional) to the pressure applied to its sensing surface 1212. Similarly, the acoustic transducer 1206 comprises a piezoelectric (ceramic) device which is capable of both generating and receiving acoustic waves and/or pulses depending on mode. In the illustrated embodiment, the acoustic transducer 1206 is tuned to generate ultrasonic frequencies centered at 8 MHz, although other center frequencies, with varying bandwidths, may be used. The signal generator/receiver 1210 generates electrical signals or pulses which are provided to the acoustic transducer 1206 and converted into acoustic energy radiated into the blood vessel. This acoustic energy is reflected by various structures within the artery, including blood flowing therein, as well as tissue and other bodily components in proximity to the artery. These acoustic reflections (echoes) are received by the acoustic transducer 1206 and converted into electrical signals which are then converted by the signal generator/receiver 1210 to a digital form (using, e.g., an ADC) and sent to the signal processor 1208 for analysis. Depending on the type of acoustic analysis technique and mode employed, the signal processor 1208 utilizes its program (either embedded or stored in an external storage device) to analyze the received signals. For example, if the system is used to measure the maximum blood velocity, then the received echoes are analyzed for, inter alia, Doppler frequency shift. Alternatively, if the arterial diameter (area) is measured, then an analysis appropriate to the aforementioned A-mode is employed.

During a calibration "sweep", the controller 1211 controls the applanation device to applanate the artery (and interposed tissue) according to a predetermined profile. During this sweep, acoustic signals are transmitted into and received from the artery preferably in a region directly proximate the ongoing applanation of the tissue. Velocity, kinetic energy, and/or arterial diameter data is extracted and/or derived from the received echoes and recorded as a function of the applanation pressure for the selected portion(s) of the cardiac cycle. The signal processor 1208 and associated algorithms then identify one or more markers, and determine the desired applied pressure at which continuous monitoring is to occur based on the measured markers. For example, if the peak in maximum velocity shown in FIG. 4b were selected as the marker, the algorithms would identify this peak and identify the pressure data corresponding to this peak. During subsequent blood pressure monitoring, the controller 1211 would servo the position of the applanation device 1204 (in the present embodiment, the pressure transducer 1202) so as to maintain the target pressure, or any other value selected by the programmer/user. Subsequent changes in the measured parameter (e.g., total blood flow kinetic energy) are used to identify changes in the actual blood pressure within the artery, thereby obviating the need for a continuing series of calibration sweeps.

Optionally, the apparatus 1200 is also configured to measure the transfer function of the tissue and other bodily components interposed between the signal source and the sensor. As described with respect to FIG. 7 above, there is an incomplete or fractional transfer of energy between the blood within the artery and the pressure sensor. To address this issue, the apparatus 1200 of FIG. 12 includes a transfer function algorithm (not shown) which utilizes data obtained from A-mode analysis or other techniques relating to the relative compression of the arterial diameter and the proximate body components when applanated. Hence, during a calibration sweep, the apparatus 1200 stores A-mode or other comparable data which is used by the transfer function algorithm to determine the relative compression of the artery and components as a function of varying applanation pressure. The transfer function (e.g., change in arterial diameter as a function of applanation pressure) is generated by the algorithm and stored in any number of different ways, such as a look-up table or a mathematical function. Subsequent to the calibration sweep, as the apparatus 1200 servoes to the desired applied pressure derived from the identified marker, a correction is imposed on the measured pressure based on the transfer function. For example, if the system is servoing to a diastolic pressure of 60 mm Hg as measured by the pressure transducer 1202, the true value of the pressure in the artery will be corrected according to the transfer function to a value somewhat higher than 60 mm Hg.

Figure 13:
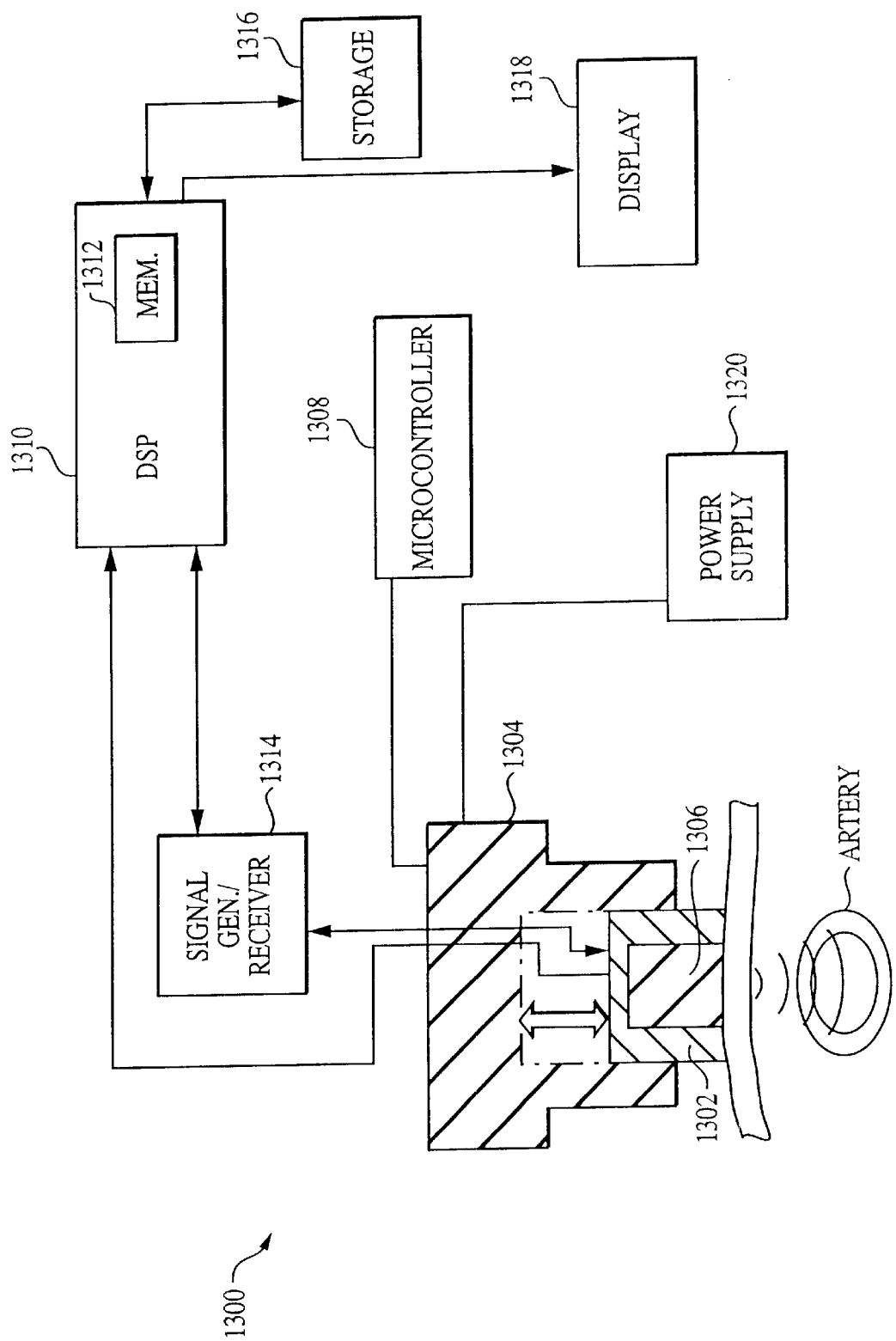
FIG. 13 is a functional block diagram of a second embodiment of the apparatus of FIG. 12 illustrating its use on the radial artery of a human being.

Referring now to FIG. 13, one specific embodiment of the apparatus for assessing hemodynamic parameters of FIG. 12 is described. In the embodiment of FIG. 13, the apparatus 1300 comprises a self-contained unit having, inter alia, a combined pressure transducer 1302 and applanation device 1304, acoustic transducer 1306, microcontroller 1308 with control micro-code (such as a fuzzy logic algorithm), digital signal processor (DSP) 1310 with embedded memory 1312 and instruction set (including calibration lookup tables), signal generator and receiver unit 1314, storage device 1316, display device 1318, and power supply 1320. In this embodiment, the microcontroller 1308 is used to control the operation of the combined pressure transducer 1302/applanation device 1304 so that an initial applanation "sweep" is performed. Specifically, the pressure transducer 1302 is placed in communication with the skin of the interior of the wrist of the subject, over the radial artery, and fastened in place as illustrated in FIG. 13. Measurement of the non-calibrated blood pressure from the radial artery is commenced, and shortly thereafter the microcontroller 1308 directs the applanation mechanism 1304 to press the transducer 1304 against the wrist of the subject with increasing pressure, thereby applanating the underlying artery. As the artery is applanated, the acoustic transducer 1306 is also pressed in communication with the skin over the artery, and the signal generator 1314 generates a series of acoustic pulses which are transmitted through the skin into the artery. As applanation of the artery continues, the signal generator/receiver unit 1314 receives echoes from the blood and other components within the artery via the acoustic transducer 1306, and generates an output signal relating to the received echoes. This output signal is processed and then digitized for subsequent analysis by the DSP or similar processing engine. Similarly, the output signal of the pressure transducer 1302 is digitized and input to the DSP. The digitized signals are then analyzed using the embedded program within the DSP, which is a machine code representation of the computer program described subsequently herein. The output of the digital signal processor is a corrected pressure waveform which is then supplied to the display device 1318 (whether in digital or analog form, depending on the type of device used) for display to the user. Optionally, the output of the DSP may be stored in one or more storage locations within the storage device 1316, and/or output to an external device.

It is noted that the apparatus 1200, 1300 described herein may be constructed in a variety of different configurations, using a variety of different components, and measuring a variety of different hemodynamic parameters. Exemplary control, signal generation/processing, and applanation mechanisms and circuitry are described in Applicant's co-pending U.S. patent application, Ser. No. 09/342,549, entitled "Method And Apparatus For The Noninvasive Determination Of Arterial Blood Pressure," previously incorporated herein.

Computer Program and Related Apparatus

Figure 14B:
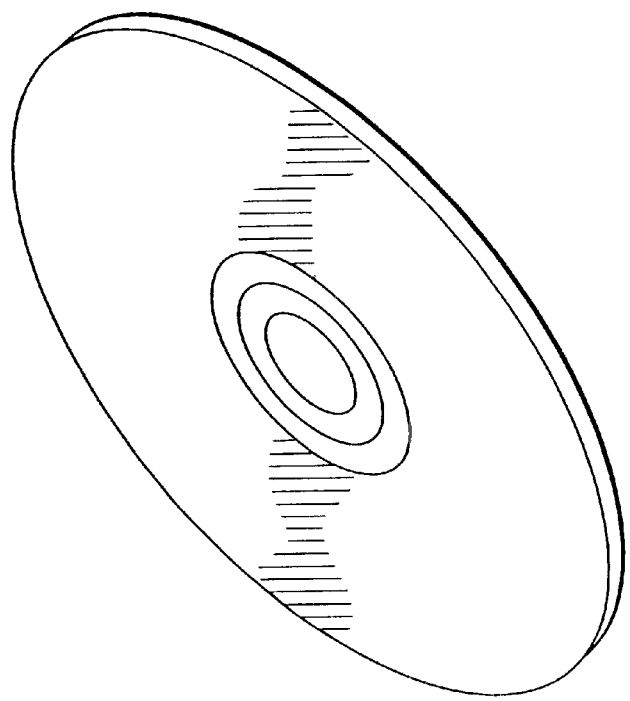
FIGS. 14a–14b are perspective views of various machine readable media having object code representations of computer programs incorporating the methods of the present invention.
Figure 14A:
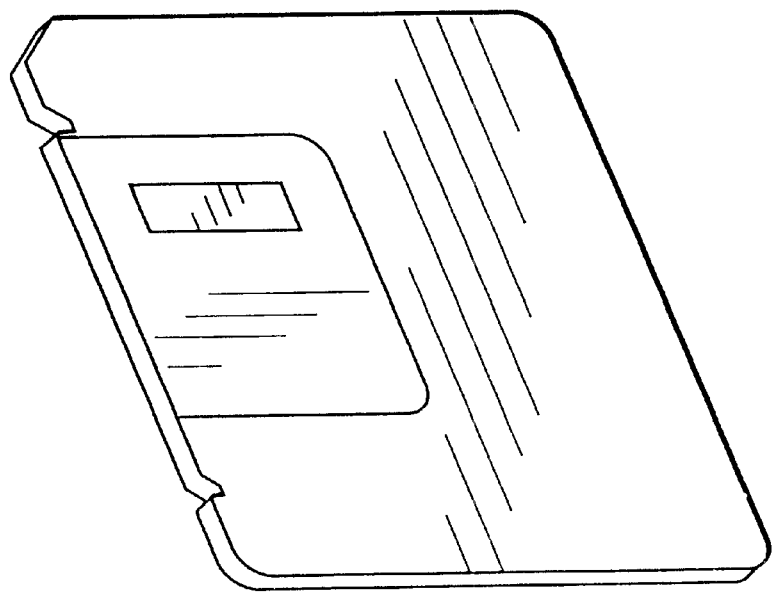

A computer program for implementing the aforementioned methods of hemodynamic assessment, modeling, and calibration is now described. In one exemplary embodiment, the computer program comprises an object ("machine") code representation of a $C^{++}$ source code listing implementing the methodology of FIGS. 3–3e, 9, and 10, either individually or in combination thereof. While $C^{++}$ language is used for the present embodiment, it will be appreciated that other programming languages may be used, including for example VisualBasic™, Fortran, and $C^+$. The object code representation of the source code listing is compiled and disposed on a media storage device of the type well known in the computer arts, as illustrated in FIGS. 14a–b. Such media storage devices can include, without limitation, optical discs, CD ROMs, magnetic floppy disks or "hard" drives, tape drives, or even magnetic bubble memory. The computer program further comprises a graphical user interface (GUI) of the type well known in the programming arts, which is operatively coupled to the display and input device of the host computer or apparatus on which the program is run (described below with respect to FIG. 15).

In terms of general structure, the program is in one embodiment comprised of a series of subroutines or algorithms for implementing the hemodynamic assessment, modeling, and calibration methodology described herein based on measured parametric data provided to the host computer. In a second embodiment, the computer program comprises an assembly language/micro-coded instruction set disposed within the embedded storage device, i.e. program memory, of a digital signal processor (DSP) or microprocessor associated with the foregoing hemodynamic measurement apparatus of FIG. 12 or 13.

Figure 15:
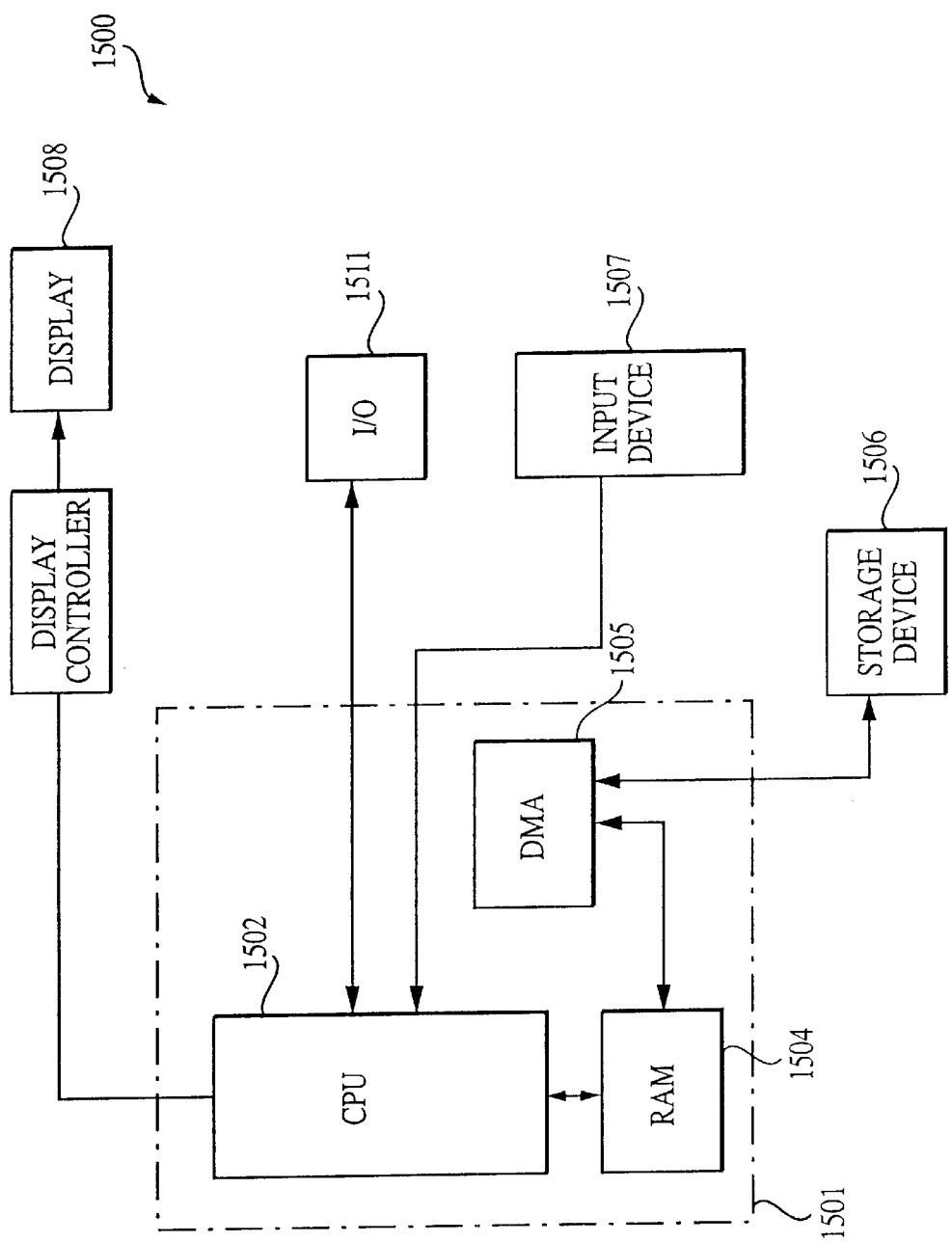
FIG. 15 is a block diagram of a first embodiment of the apparatus for analyzing parametric data according to the invention.

Referring now to FIG. 15, one embodiment of an apparatus capable of analyzing parametric data and generating calibrated values of hemodynamic parameters as disclosed herein is described. The computing device 1500 comprises a motherboard 1501 having a central processing unit (CPU) 1502, random access memory (RAM) 1504, and memory controller (such as a direct memory access controller) 1505. A storage device 1506 (such as a hard disk drive or CD-ROM), input device 1507 (such as a keyboard or mouse), and display device 1508 (such as a CRT, plasma, or TFT display), as well as buses necessary to support the operation of the host and peripheral components, are also provided. A serial or parallel I/O port 1511 is also included for the transfer of data and/or control signals to and from the apparatus 1500.

The aforementioned computer program useful for assessing hemodynamic parameters is stored in the form of a machine-readable object code representation in the RAM 1504 and/or storage device 1506 for use by the CPU 1502 during parametric assessment. The user (not shown) assesses the hemodynamic parameters of interest by selecting one or more functional modes for the computer program and associated measuring equipment via the program displays and the input device 1507 during system operation. Specifically, in the case of arterial blood pressure measurement, the user places the necessary parametric sensors on the selected blood vessel of the subject, and configures the computer program to accept data output by the sensors either continuously or at a predetermined interval. The computer program performs the previously described analysis if the signals provided to the apparatus 1500, and generates a calibrated signal to be displayed on a display device, or on the systems own display device. A look-up table or similar mechanism is stored within the computer memory or storage device to facilitate calibration, as previously described with respect to FIG. 12, Such calibrated measurements generated by the program are also optionally stored in the storage device 1506 for later retrieval, or output to an external device such as a printer, data storage unit, other peripheral component via a serial or parallel port 1512 if desired. Furthermore, the apparatus 1500 may be networked to another computing device or database via network interface card (NIC) or similar interface (not shown) whereby the data generated by the apparatus 1600 may be remotely analyzed or stored. Transmission to such remote devices may be accomplished using a variety of well understood methods, such as by local area network (LAN), intranet, Internet, fiber-optic systems, or radio frequency (wireless) devices.

In yet another embodiment, the apparatus comprises a personal computing device (such as a personal digital assistant, or PDA), which is adapted to receive input data from the pressure and acoustic sensors and analyze the data to produce a corrected measurement of blood pressure. It will also be recognized that other portable devices, such as laptop computers, calculators, and personal organizers, may be configured to run the computer program of the present invention. Furthermore, a variety of different methods of transmitting the input sensor data to these device may be used, including networked computers, or even wireless data links.

Method of Providing Treatment

Figure 16:
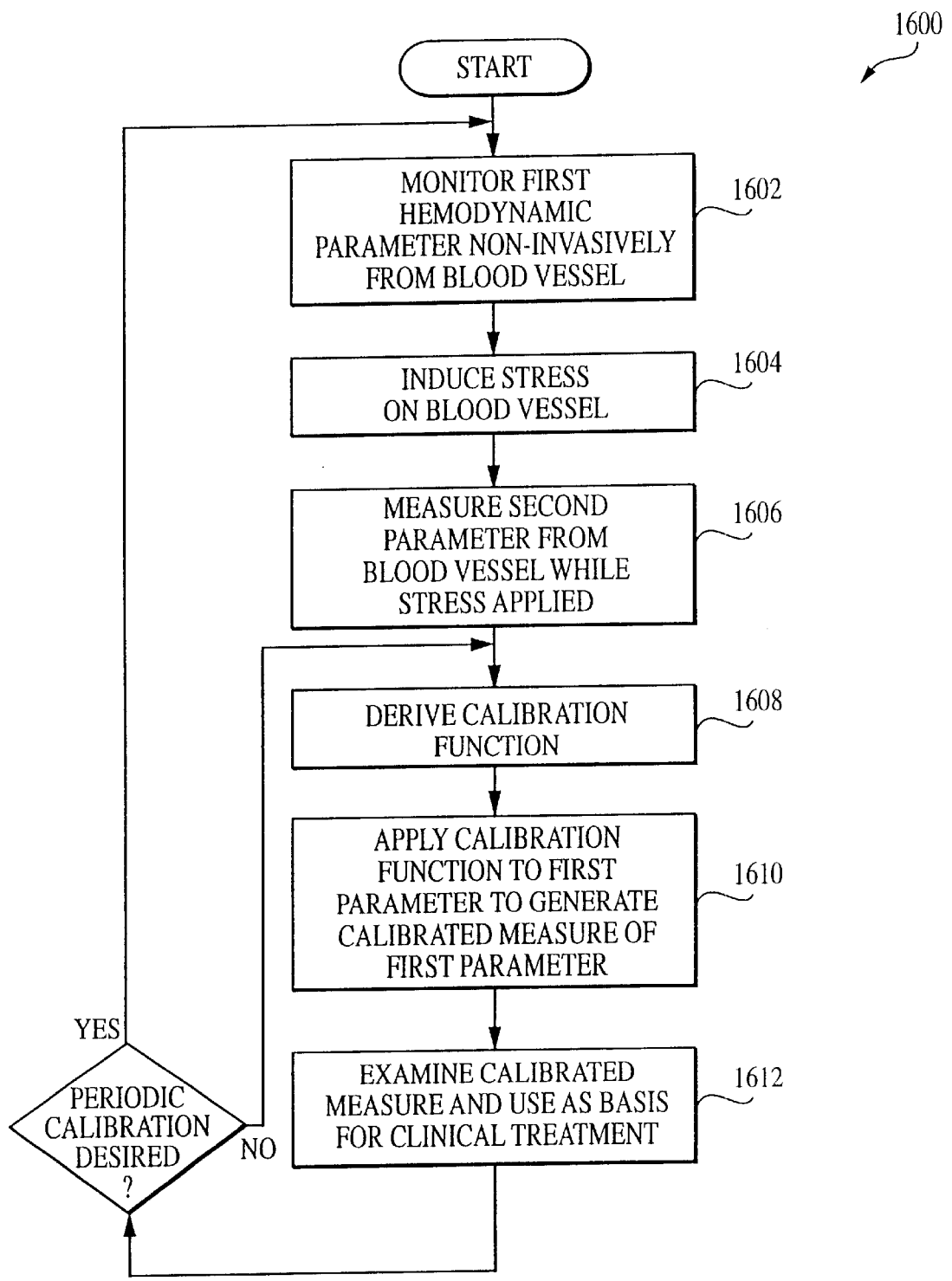
FIG. 16 is a logical flow diagram illustrating one exemplary embodiment of the method of providing treatment to a subject using the aforementioned methods.

Referring now to FIG. 16, a method of providing treatment to a subject using the aforementioned method of assessing hemodynamic parameters is disclosed. As illustrated in FIG. 16, the first step 1602 of the method 1600 comprises monitoring an non-calibrated hemodynamic parameter non-invasively. In the case of blood pressure, an exemplary pressure transducer applied to the radial artery is used as described with respect to FIG. 3a herein.

Next, in step 1604 of FIG. 16, a stress is induced on the blood vessel which alters its hemodynamic properties (at least locally), thereby inducing changes in other parameters associated with the vessel or circulatory system as a whole. As previously discussed with respect to FIG. 3b herein, this stress comprises in one embodiment applanating or variably compressing the blood vessel as a function of time, thereby inducing changes in, inter alia, the volumetric flow (Q), velocity (v), and kinetic energy (KE) of the blood in the region of the applanation. It is again noted, however, that other stressors may conceivably be applied which may affect similar or other hemodynamic properties.

Next, in step 1606, a second parameter associated with the blood vessel is measured in order to facilitate derivation of a calibration function in step 1608 below. As discussed with respect to FIG. 3c herein, the second parameter in one embodiment comprises total blood flow kinetic energy or maximum blood velocity since these parameter exhibits certain easily identified "artifacts" as a function of the application of the stressor in step 1604. Other parameters which exhibit the same or other artifacts may be used to derive the calibration function however.

In step 1608 of FIG. 16, a calibration metric or function is next derived based on the parametric information derived in step 1606. Specifically, one or more artifacts or markers are identified within the parametric data, these artifacts indicating when certain relationships between the actual and measured values of the first parameter of step 1602 above exist. As discussed with reference to FIGS. 3–3e herein, one embodiment of the process of deriving a calibration function comprises (i) measuring kinetic energy or maximum blood velocity profiles proximate to the area of the applied stressor (applanation), and identifying regions of increasing velocity or kinetic energy within these profiles as a function of the applanation (correlated to percentage reduction of cross-sectional area of the blood vessel); and (ii) measuring a transfer function for the tissue and other bodily components in the region of pressure measurement.

In step 1610 of the method of FIG. 16, the calibration function derived in step 1608 is applied to the measurement of the first parameter of step 1602 to generate a corrected or calibrated measurement. Note that if the first parameter is measured continuously (or periodically) as a function of time, the correction function of step 1608 may be continuously or periodically applied as appropriate, or alternatively the second hemodynamic parameter may be monitored (such as during pressure servoing as previously described) to indicate changes in the calibration function.

Lastly, in step 1612, the calibrated measurement of the first parameter is used as the basis for providing treatment to the subject. For example, in the case of blood pressure measurements, the calibrated systolic and diastolic blood pressure values are generated and displayed or otherwise provided to the health care provider in real time, such as during surgery. Alternatively, such calibrated measurements may be collected over an extended period of time and analyzed for long term trends in the condition or response of the circulatory system of the subject.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of assessing hemodynamic properties within the circulatory system of a living subject, comprising:
    measuring a first parameter from a blood vessel of said subject;
    compressing said blood vessel, and measuring a second parameter from said blood vessel during at least a portion of said act of compressing;
    identifying at least one artifact within said second parameter;
    generating a calibration function based at least in part on said at least one artifact; and
    calibrating the first parameter using at least said calibration function.

2. The method of claim 1, wherein the act of measuring a second parameter comprises;
    transmitting an acoustic wave into said blood vessel;
    receiving at least one echo of said acoustic wave; and
    analyzing said at least one echo to derive an estimate of said second parameter.

3. The method of claim 2, wherein said second parameter comprises blood velocity, and the act of identifying at least one artifact comprises identifying a predetermined variation in maximum blood velocity.

4. The method of claim 2, wherein said second parameter is related to blood velocity, and the act of identifying at least one artifact comprises identifying a maximum value within said second parameter.

5. The method of claim 1, wherein said act of compressing comprises compressing said blood vessel according to an applanation profile.

6. The method of claim 5, wherein said profile comprises modulating the position of said at least one transducer as a function of time.

7. The method of claim 1, wherein said first parameter comprises pressure, and said second parameter is related to blood flow velocity.

8. A method of assessing hemodynamic properties within the circulatory system of a living subject, comprising:
    measuring a pressure waveform from a blood vessel of said subject using at least one transducer;
    compressing said blood vessel using said at least one transducer, and measuring a parameter from said blood vessel during at least a portion of said act of compressing;
    identifying at least one artifact within said parameter;
    generating a calibration function based at least in part on said at least one artifact; and
    calibrating the pressure waveform using at least said calibration function.

9. The method of claim 8, wherein said parameter comprises blood velocity, and the act of identifying at least one artifact comprises identifying a predetermined variation in maximum blood velocity.

10. The method of claim 8, wherein said parameter comprises blood flow kinetic energy.

11. The method of claim 8, wherein said act of compressing comprises compressing said blood vessel according to an applanation profile.

12. The method of claim 11, wherein said profile comprises modulating the position of said at least one transducer as a function of time.

13. A method of assessing hemodynamic properties within the circulatory system of a living subject, comprising:
    measuring a first parameter from a blood vessel of said subject;
    compressing said blood vessel, and measuring from said vessel the kinetic energy of blood flowing therein during at least a portion of said act of compressing;
    deriving a calibration function based at least in part on said kinetic energy; and
    calibrating the first parameter using said calibration function.

14. The method of claim 12, wherein the act of measuring the kinetic energy comprises:
    measuring the Doppler shift associated with the blood flowing within the blood vessel; and
    calculating the mean kinetic energy of said blood based on said Doppler shift.

15. A method of assessing hemodynamic properties within the circulatory system of a living subject, comprising:
    measuring a first parameter from a blood vessel of said subject;
    compressing said blood vessel. and measuring the diameter of said blood vessel during at least a portion of said act of compressing;
    deriving a calibration function based at least in part on said diameter; and
    calibrating the first parameter using said calibration function.

16. The method of claim 15, wherein the act of measuring said diameter comprises:
    transmitting an acoustic wave into said blood vessel;
    receiving at least one echo from said acoustic wave; and
    analyzing said at least one echo to determine the arterial diameter.

17. The method of claim 16, wherein said acoustic wave comprises an A-mode acoustic transmission.

18. The method of claim 16, wherein said acoustic wave comprises an M-mode (motion-mode) acoustic transmission.

19. The method of claim 16, wherein said acoustic wave comprises a B-mode (brightness mode) acoustic transmission.

20. The method of claim 15, wherein said act of deriving a calibration function comprises identifying at least one artifact during said act of measuring said diameter, and generating said calibration function based at least in part on said at least one artifact.

21. The method of claim 20, wherein said act of identifying at least one artifact comprises identifying the level of compression at which the cross-sectional area of said blood vessel is maximized.

22. A method of assessing hemodynamic properties within the circulatory system of a living subject, comprising:
measuring a first parameter from a blood vessel of said subject;
compressing said blood vessel, and measuring the volumetric flow rate associated with at least a portion of said blood vessel during at least a portion of said act of compressing;
deriving a calibration function based at least in part on said volumetric flow rate; and
calibrating the first parameter using said calibration function.

23. The method of claim 22, wherein said first parameter comprises pressure, and said act of deriving a calibration function comprises identifying at least one artifact within a compression/volumetric flow rate profile, and deriving a scaling function based at least in part on the pressure measured at the point where said at least one artifact occurs.

24. A method of assessing hemodynamic properties within the circulatory system of a living subject, comprising:
measuring a first parameter from a blood vessel of said subject;
compressing said blood vessel, and measuring a second parameter from said blood vessel during at least a portion of said act of compressing;
measuring the actual compression of said blood vessel during at least a portion of said act of compressing;
generating a transfer function indicative of said actual compression;
deriving a calibration function based at least in part on said second parameter and said transfer function; and
calibrating the first parameter using said calibration function.

25. The method of claim 24, wherein said act of generating a transfer function comprises generating at least one function relating level of compression and flow area.

26. The method of claim 24, wherein said act of generating a transfer function comprises generating separate functions for systolic and diastolic conditions.

27. A method of measuring the pressure within the circulatory system of a living subject, comprising:
measuring a non-calibrated pressure from a blood vessel of said subject;
measuring a second parameter from said blood vessel;
creating a stress on said blood vessel during at least a portion of the act of measuring said second parameter, said stress producing a known effect on said second parameter, the application of said stress being selectively controlled so as to maintain a predetermined condition within said blood vessel;
identifying at least one marker within said measurement of said second parameter, said at least one marker being related to said known effect;
deriving a calibration function based at least in part on said at least one marker; and
correcting said non-calibrated pressure using the derived calibration function.

28. The method of claim 27, wherein the act of measuring a second parameter comprises measuring said second parameter using an acoustic wave, and the act of creating a stress comprises variably compressing said blood vessel as a function of time.

29. The method of claim 28, wherein said predetermined condition comprises maintaining the pressure across the wall of the blood vessel within a predetermined range.

30. The method of claim 27, wherein said predetermined condition comprises maintaining the pressure across the wall of the blood vessel within a predetermined range.

31. A method of measuring the pressure within the circulatory system of a living subject, comprising:
measuring a non-calibrated pressure from a blood vessel of said subject;
measuring the velocity of blood flowing within said blood vessel using an acoustic wave and by forming a time-frequency representation from echoes of said acoustic wave;
variably compressing said blood vessel as a function of time during at least a portion of the act of measuring said velocity, said compressing producing a known effect on said velocity;
identifying at least one marker within said measurement of said velocity, said at least one marker being related to said known effect;
deriving a calibration function based at least in part on said at least one marker; and
correcting said non-calibrated pressure using the derived calibration function.

32. A method of measuring the pressure within the circulatory system of a living subject, comprising:
measuring a non-calibrated pressure waveform from a blood vessel of said subject;
determining the velocity of blood flowing within said blood vessel at least in part by forming a time-frequency representation from echoes of acoustic waves transmitted into said blood vessel;
variably compressing said blood vessel as a function of time during at least a portion of the act of determining said velocity, said compressing producing a known effect on said velocity;
identifying at least one marker within said determination of said velocity, said at least one marker being related to said known effect;
deriving a calibration function based at least in part on said at least one marker; and
correcting said non-calibrated pressure waveform using the derived calibration function.

33. A method of measuring the pressure within the circulatory system of a living subject, comprising:
measuring a non-calibrated pressure from a blood vessel of said subject;
measuring the velocity of blood flowing within said blood vessel using an acoustic wave;

forming a time-frequency representation from echoes of said acoustic wave;

variably compressing said blood vessel as a function of time during at least a portion of the act of measuring said velocity, said compressing producing a known effect on said velocity;

identifying at least one marker within said measurement of said velocity, said at least one marker being related to said known effect, said act of identifying being based at least in part on said time-frequency representation;

deriving a calibration function based at least in part on said at least one marker; and correcting said non-calibrated pressure using the derived calibration function.

34. An apparatus for measuring hemodynamic properties within the radial artery of a human subject comprising:

a pressure transducer adapted to be located proximate said artery and measure at least a pressure waveform therefrom;

an acoustic transducer adapted to measure at least one hemodynamic parameter associated with said artery;

an applanation device adapted to compress at least a portion of said artery while measuring said at least one hemodynamic parameter; and a signal processor operatively connected to said pressure and acoustic transducers and configured to generate a calibration function based at least in part on a signal produced by said acoustic transducer, and apply said calibration function to a signal produced by said pressure transducer.

35. The apparatus of claim 34, wherein said acoustic transducer transmits at least one acoustic emission into said artery and receives at least one echo therefrom, said at least one echo being used by said signal processor to generate a relationship between said at least one hemodynamic parameter and the pressure applied by said applanation device.

36. The apparatus of claim 34, wherein said applanation device comprises said pressure transducer.

37. The apparatus of claim 35, wherein said at least one acoustic emission comprises an acoustic pulse.

38. The apparatus of claim 35, wherein said at least one acoustic emission comprises a substantially continuous acoustic wave.

39. The apparatus of claim 34, wherein said at least one hemodynamic parameter comprises the maximum velocity of blood flowing within said artery.

40. The apparatus of claim 34, wherein said at least one hemodynamic parameter comprises the amplitude-weighted mean velocity of blood flowing within said artery.

41. The apparatus of claim 34, wherein said at least one hemodynamic parameter is related to the kinetic energy of blood flowing within said artery.

42. An information storage device, comprising;

a data storage medium;

a plurality of data stored on said medium, said plurality of data comprising a computer program adapted to run on a data processor, said computer program being configured for determining a calibrated value of a first hemodynamic parameter of a living subject based on first, second, and third input data, said first input data being representative of a non-calibrated value of said first hemodynamic parameter, said second input data being representative of a second hemodynamic parameter, said third input data relating to the error associated with said first input data, the act of determining said calibrated value of said first hemodynamic parameter comprising:

analyzing said second input data to identify at least one functional relationship therein;

identifying at least one marker within said at least one functional relationship;

determining a calibration function based at least in part on said at least one marker and said third data; and applying said calibration function to said first input data to determine said calibrated value.

43. An information storage device, comprising;

a data storage medium;

a plurality of data stored on said medium, said plurality of data comprising a computer program adapted to run on a data processor, said computer program being configured for determining a calibrated value of a first hemodynamic parameter of a living subject based on first input data and second input data, said first input data being representative of a non-calibrated value of said first hemodynamic parameter, said second input data being representative of a second hemodynamic parameter, the act of determining said calibrated value of said first hemodynamic parameter comprising:

forming a time-frequency distribution from said second input data;

analyzing at least said time-frequency distribution to identify at least one artifact therein;

utilizing said at least one artifact to derive a calibration function; and applying said calibration function to said first input data to determine said calibrated value.

* * * * *